US012778611B2

(12) United States Patent
Eisenfrats et al.

(10) Patent No.: US 12,778,611 B2
(45) Date of Patent: Nov. 3, 2026

(54) SYSTEMS AND METHODS FOR REMOVING A HYDROGEL IMPLANT FROM A BODY LUMEN

(71) Applicant: CONTRALINE, INC., Charlottesville, VA (US)

(72) Inventors: Kevin Eisenfrats, Charlottesville, VA (US); Tyler Chiartas, Charlottesville, VA (US); Nicholas Matsumoto, Charlottesville, VA (US); Yelena Tropsha, Plymouth, MN (US); Jeffrey W. Ference, Barboursville, VA (US)

(73) Assignee: Contraline, Inc., Charlottesville, VA (US)

( * ) Notice: Subject to any disclaimer, the term of this patent is extended or adjusted under 35 U.S.C. 154(b) by 2 days.

(21) Appl. No.: 19/120,974

(22) PCT Filed: Oct. 24, 2023

(86) PCT No.: PCT/US2023/035796
§ 371 (c)(1),
(2) Date: Apr. 14, 2025

(87) PCT Pub. No.: WO2024/091496
PCT Pub. Date: May 2, 2024

(65) Prior Publication Data

US 2026/0144557 A1 May 28, 2026

Related U.S. Application Data

(60) Provisional application No. 63/529,786, filed on Jul. 31, 2023, provisional application No. 63/419,145, filed on Oct. 25, 2022.

(51) Int. Cl.
*A61B 17/22* (2006.01)
*A61B 17/12* (2006.01)

(52) U.S. Cl.
CPC .... *A61B 17/22031* (2013.01); *A61B 17/1219* (2013.01); *A61B 2017/22038* (2013.01);
(Continued)

(58) Field of Classification Search
CPC .......... A61B 17/22031; A61B 17/1219; A61B 2017/22038; A61B 2017/22072;
(Continued)

(56) References Cited

U.S. PATENT DOCUMENTS

2004/0158270 A1 8/2004 Wyzgala et al.
2007/0163601 A1 7/2007 Pollock et al.
(Continued)

FOREIGN PATENT DOCUMENTS

WO WO2021243046 12/2021
WO WO-2021243046 A1 * 12/2021 ......... A61B 18/1492

OTHER PUBLICATIONS

Invitation to Pay Additional Fees for PCT/US2023/035796, mailed Jan. 17, 2024.
(Continued)

*Primary Examiner* — Richard G Louis
(74) *Attorney, Agent, or Firm* — Mills IP Law, PLLC

(57) ABSTRACT

Methods for removing a biomaterial implant and reversing occlusive effects of the biomaterial implant are described. In particular, methods for performing removal of biomaterial implants without damage to a body lumen where the biomaterial was previously implanted are presented. More specifically, methods of reversing an implant within a vas deferens are described.

6 Claims, 17 Drawing Sheets

(52) U.S. Cl.
CPC ............... *A61B 2017/22072* (2013.01); *A61B 2217/007* (2013.01)

(58) Field of Classification Search
CPC ............ A61B 2217/007; A61B 17/221; A61B 17/22012; A61B 17/32037; A61B 2017/00893; A61B 2017/00898; A61F 6/22
See application file for complete search history.

(56) References Cited

U.S. PATENT DOCUMENTS

| | | | |
|---|---|---|---|
| 2008/0071269 | A1 | 3/2008 | Hilario et al. |
| 2013/0220335 | A1 | 8/2013 | Lee-Sepsick et al. |
| 2014/0261446 | A1 | 9/2014 | Sjoquist et al. |
| 2017/0014153 | A1 | 1/2017 | To et al. |
| 2018/0092661 | A1 | 4/2018 | Prabhu |
| 2018/0185096 | A1 | 7/2018 | Eisenfrats et al. |
| 2019/0038454 | A1 | 2/2019 | Eisenfrats et al. |
| 2019/0099280 | A1 | 4/2019 | Ben Muvhar |
| 2019/0142453 | A1 | 5/2019 | Efremkin |
| 2020/0237388 | A1 | 7/2020 | Eisenfrats et al. |
| 2022/0168036 | A1 | 6/2022 | Wei |
| 2023/0346589 | A1* | 11/2023 | Grover .................. A61L 31/145 |

OTHER PUBLICATIONS

International Search Report and Written Opinion for PCT/US2023/035796, mailed Mar. 5, 2024.

* cited by examiner

SYSTEMS AND METHODS FOR REMOVING A HYDROGEL IMPLANT FROM A BODY LUMEN

CROSS-REFERENCE TO RELATED APPLICATIONS

This application is a U.S. national stage filing under 35 U.S.C. § 371 of International Application No. PCT/US2023/035796, entitled "Systems and Methods for Removing a Hydrogel Implant from a Body Lumen." filed Oct. 24, 2023, which claims priority to and the benefit of U.S. Provisional Patent Application No. 63/419,145, entitled "Systems and Methods for Removing a Hydrogel Implant From a Body Lumen," filed Oct. 25, 2022, and U.S. Provisional Patent Application No. 63/529,786, entitled "Systems and Methods for Removing a Hydrogel Implant From a Body Lumen," filed Jul. 31, 2023, the disclosures of which are incorporated by reference in their entirety.

BACKGROUND

The embodiments described herein relate generally to methods and systems for removing biomaterials, and more particularly to removal of hydrogel implants from a body lumen.

Biomaterials are natural or synthetic materials (such as polymers) that are suitable for introduction into living tissues as therapeutics (to treat, augment, repair, modify, or replace a tissue function of the body) or as diagnostics. Biomaterials such as hydrogel implants have been shown to be useful for embolization, drug delivery, sealing, filling, and occlusion purposes. Hydrogels are highly hydrated polymer chains or networks that are able to absorb significant volumes of water and can have tunable mechanical properties. Biomaterials are often injectable, such as through a needle and/or catheter into the body. When injected, the material may gel or cross-link to form the implant.

Some known systems and methods include injecting and/or implanting a biomaterial product (e.g., a hydrogel) into a small area such as the lumen of a vessel or duct. For example, in some applications, the biomaterial will form an implant that acts as an occlusion or embolization of a lumen. The occlusion can be used for providing contraception to a subject and/or for reducing fertility and/or inducing infertility of the subject by occluding the vas deferens, fallopian tube(s), or uterus. Such occlusions can also be used to occlude any other body part, such as ducts, tissues, interstitial spaces, or organs such as for drug delivery, spacing, sealing, embolizing, or bulking purposes.

For contraceptive applications, there are currently no long acting, reversible contraceptives available for males on the market. For example, while vasectomy is long acting for contraceptive purposes, the procedure is generally considered permanent due to the difficulty in reversing the process. Even when the reversal procedure is correctly performed, patients often have low rates of fertility following reversal. By way of another example, a biomaterial may be implanted within the vas deferens to occlude the vas deferens. A surgical procedure can be performed where the vas deferens is cut along a location of the implant, the implant is removed, and the vas deferens is sutured back together. However, such a surgical removal procedure can be technically challenging, may have significant complications including long-term recovery and/or potential damage to the vas deferens (which may be irreversible) and may not restore sperm parameters comparable to pre-implant baseline levels. In some known systems and methods where a biomaterial is implanted to occlude the vas deferens, the implant can be reversed by supplying a chemical solution to dissolve the implant within the vas deferens. However, such systems and methods require high volumes of dissolving agents, where the dissolving agent may be toxic, and also typically do not restore sperm parameters comparable to pre-implant baseline levels. Sperm parameters may include sperm concentration, total motility, progressive motility, morphology, and/or viability and/or other biomarkers of sperm function/fertility.

Thus, a need exists for systems and methods of removing biomaterial implants from a reproductive system to restore functionality/patency as well as fertility and/or sperm parameters of a patient to levels similar to those prior to the implantation of the biomaterial. A need further exists for a removal procedure that can be performed in a short time frame without the need for microsurgery or suturing, where the procedure has consistent and repeatable results. A need further exists for systems and methods to be performed in a safe, minimally invasive manner to reduce recovery time of the patient following the removal procedure and to allow the patient to have multiple implants and reversals throughout their lifetime.

SUMMARY

Systems and methods for removing a biomaterial implant and reversing occlusive effects of the biomaterial implant are described herein. In particular, methods for performing removal of biomaterial implants without damage to a body lumen where the biomaterial was previously placed are described. For example, the systems and methods described herein can be employed to remove biomaterial implants from a body lumen (e.g., a vas deferens) that has an internal diameter of less than 15 mm (e.g., 10 mm or less).

In some embodiments, a method of removing an implant from a body lumen includes inserting a delivery member into a first body lumen (e.g., a vas deferens). The delivery member is in fluid communication with the implant. A force is then exerted on the implant via the delivery member, and at least a portion of the implant is moved from the first body lumen via the force.

In some embodiments, a method of removing an implant from a body lumen includes inserting a delivery member into a first body lumen (e.g., a vas deferens). The delivery member is in fluid communication with an upstream portion of the implant. A force is exerted on the upstream portion of the implant, facilitated by the delivery member. In response to the force, the implant is moved downstream or upstream in the direction of a second body lumen or organ (e.g., a urethra or a bladder). In some embodiments, the force is exerted on an undisturbed (e.g., intact) implant. However, in some embodiments, the structural integrity of the implant is mechanically disrupted prior to exerting the force on the upstream portion of the implant. In further embodiments, the structural integrity of the implant is chemically disrupted prior to exerting the force on the upstream portion implant.

In some embodiments, prior to exerting the force on the upstream portion of the implant, a guidewire is advanced through the delivery member and through or around the implant. A microcatheter is advanced over the guidewire and through or around the implant to position a distal end portion of the microcatheter downstream of the implant. A retrieval tool is then advanced through the microcatheter to a position that is downstream of the distal end portion of the microcatheter. The retrieval tool is then transitioned to an expanded configuration and a portion of the implant is engaged. The portion of the implant is extracted from the first body lumen by moving the retrieval tool in an upstream or downstream direction.

In some embodiments, exerting the force on the upstream portion of the implant includes advancing an expandable member into the first body lumen. The expandable member is transitioned to an expanded configuration and advanced in a downstream direction. Advancing the expandable member in the downstream direction exerts the force on the upstream portion of the implant.

In some embodiments, following the exertion of the force on the upstream portion of the implant, a flush solution is conveyed into the body lumen. The flush solution conveys a remnant of the implant downstream towards the second body lumen.

In some embodiments, a method of removing an implant from a body lumen includes inserting a delivery member into a first body lumen. The delivery member is in fluid communication with the implant. The method includes delivering a first removal fluid to the implant via the delivery member at a delivery pressure to cause an eroded portion of the implant to be separated from a remnant portion of the implant and flushing the eroded portion of the implant in an upstream direction of the first body lumen. The method also includes delivering a second removal fluid, after the flushing of the eroded portion of the implant in the upstream direction, to move the remnant portion of the implant downstream to a second body lumen.

In some embodiments, the delivery pressure is less than a burst pressure of the first body lumen.

In some embodiments, the method includes adjusting the delivery pressure based at least in part on a length and/or a width of the implant within the first body lumen.

In some embodiments, delivering the first removal fluid includes delivering a delivery volume of the first removal fluid, and the method includes determining a delivery volume of the first removal fluid based at least in part on a length of the implant within the first body lumen.

In some embodiments, the method includes heating the first removal fluid to a delivery temperature prior to delivering the first removal fluid, the delivery temperature being greater than 35 degrees Celsius and less than 65 degrees Celsius.

In some embodiments, the method includes determining a mass of the implant. For example, the method can include capturing the eroded portion of the implant flushed in the upstream direction upon exit from the first body lumen and determining a mass of the remnant portion of the implant based on the mass of the implant and a mass of the eroded portion. Additionally, the method includes delivering the second removal fluid when the mass of the remnant portion is below a threshold magnitude.

In some embodiments, the method includes determining a length of the implant (e.g., an overall length of the implant). For example, the method can include advancing the delivery member within the first body lumen and into contact with the implant prior to delivering the first removal fluid and determining a first insertion length of the delivery member on a condition that the delivery member is in contact with the implant prior to delivering the first removal fluid. Additionally, the method includes determining a second insertion length of the delivery member on a condition that the delivery member is in contact with the implant after the separation of the eroded portion of the implant. The method also includes determining a remnant length based on the length of the implant, the first insertion length, and the second insertion length and delivering the second removal fluid when the remnant length is below a threshold magnitude.

In some embodiments, the first removal fluid is a saline solution.

In some embodiments, the first removal fluid includes at least one of sodium bicarbonate, dimethyl sulfoxide, aqueous solution(s) (neutral, basic, or acidic), solution(s) containing oxidative or antioxidative compounds, solution(s) containing dissolved gases, lubricious solution(s), surfactant(s), inorganic compound(s), organic solvent(s), aqueous-organic mixture(s), emulsifier(s), lipid(s), phospholipids(s), enzyme(s), protein(s), peptide(s), polynucleotide(s), saccharides(s), polysaccharide(s), small organic molecule(s), large organic molecule(s), nanoparticle(s), microparticle(s), quantum dot(s), carbon-based material(s), and/or any combination thereof.

In some embodiments, the delivery member is one of a microcatheter or a hypo tube.

In some embodiments, the delivery member includes at least one flow element configured to modify the flow of the first removal fluid within the delivery member.

In some embodiments, the delivery member has a maximal outer diameter of less than or equal to 1.0 millimeters and greater than or equal to 0.5 millimeters.

In some embodiments, the delivery member includes a distal end portion. The distal end portion defines a longitudinal axis, a distal orifice that is axially aligned with the longitudinal axis, and at least one radial orifice positioned proximal to the distal orifice. The delivering the first removal fluid includes delivering a portion of the first removal fluid via the at least one radial orifice such that the portion of the first removal fluid is directed radially outward from the longitudinal axis.

In some embodiments, the delivery member is a dual-lumen delivery member having a first member lumen extending along a longitudinal length of the delivery member and a second member lumen extending along the longitudinal length of the delivery member.

In some embodiments, the second member lumen surrounds the first member lumen.

In some embodiments, the first member lumen and the second member lumen are arranged in a side-by-side configuration.

In some embodiments, the delivering the first removal fluid is performed via the first member lumen. The flushing of the eroded portion of the implant includes delivering a flush fluid via the second member lumen during the delivery of the first removal fluid via the first member lumen.

In some embodiments, the delivering the first removal fluid is performed via the first member lumen. In such embodiments, the method includes aspirating the eroded portion of the implant via the second member lumen during the delivery of the first removal fluid via the first member lumen.

In some embodiments, the method includes mechanically disrupting a structural integrity of the implant during delivery of the first removal fluid.

In some embodiments, the mechanically disrupting the structural integrity of the implant includes positioning a distal end portion of the delivery member at an initial position in contact with the implant, moving the distal end portion in a distal direction from the initial position into the implant to a delivery position, and oscillating the distal end portion between the initial position and the delivery position to mechanically disrupt the structural integrity of the implant during delivery of the first removal fluid.

In some embodiments, the delivery member is operably coupled to a control device, and the control device includes at least one sensor configured to monitor an operating condition of a distal end portion of the delivery member.

In some embodiments, the sensor(s) of the control device is an accelerometer, and the method includes limiting a flow of the first removal fluid in response to a signal from the accelerometer indicating that the distal end portion of the delivery member is stationary.

In some embodiments, the sensor(s) of the control device is a load sensor. The load sensor is configured to detect a condition in which the distal end portion is in contact with the implant based at least in part on a stiffness of the implant. The control device produces an indication of contact between the distal end portion and the implant based on the detection by the load sensor.

In some embodiments, inserting the delivery member into the first body lumen includes inserting the delivery member through an incision in the first body lumen. The incision has a length that is at least two times an outer diameter of the delivery member.

In some embodiments, the method includes establishing an entry orifice in the first body lumen at a location that is upstream of the implant. The entry orifice is sized to receive the delivery member. The method also includes establishing an exit orifice in the first body lumen at a location that is upstream of the implant and downstream of the entry orifice. The exit orifice is sized to facilitate passage of the eroded portion of the implant.

In some embodiments, inserting the delivery member into the first body lumen includes inserting the delivery member through a cannula positioned partially in the first body lumen. The cannula has an inner diameter that is sized to receive an outer diameter of the delivery member and permit passage of the eroded portion of the implant on a condition that the delivery member is inserted into the first body lumen.

In some embodiments, the implant has a storage moduli greater than about 1000 Pascals.

In some embodiments, an apparatus for the removal of an implant from a lumen includes a delivery member sized to be received by a cannula and inserted into a first lumen. The delivery member is in fluid communication with an implant within the first lumen on a condition that the delivery member is inserted into the first lumen. A fluid reservoir is fluidically coupled to the delivery member. A removal fluid is contained by the fluid reservoir. The removal fluid is configured to be delivered to the implant via the delivery member at a delivery pressure to cause an eroded portion of the implant to be separated from a remnant portion of the implant. The removal fluid is also configured to flush the eroded portion of the implant in an upstream direction of the first lumen. Additionally, the removal fluid is configured to move the remnant portion of the implant downstream to a second lumen following the eroding of the eroded portion.

The description below and the accompanying figures will provide greater details on the various systems, methods for removing biomaterial implants.

DETAILED DESCRIPTION

Figure 1:
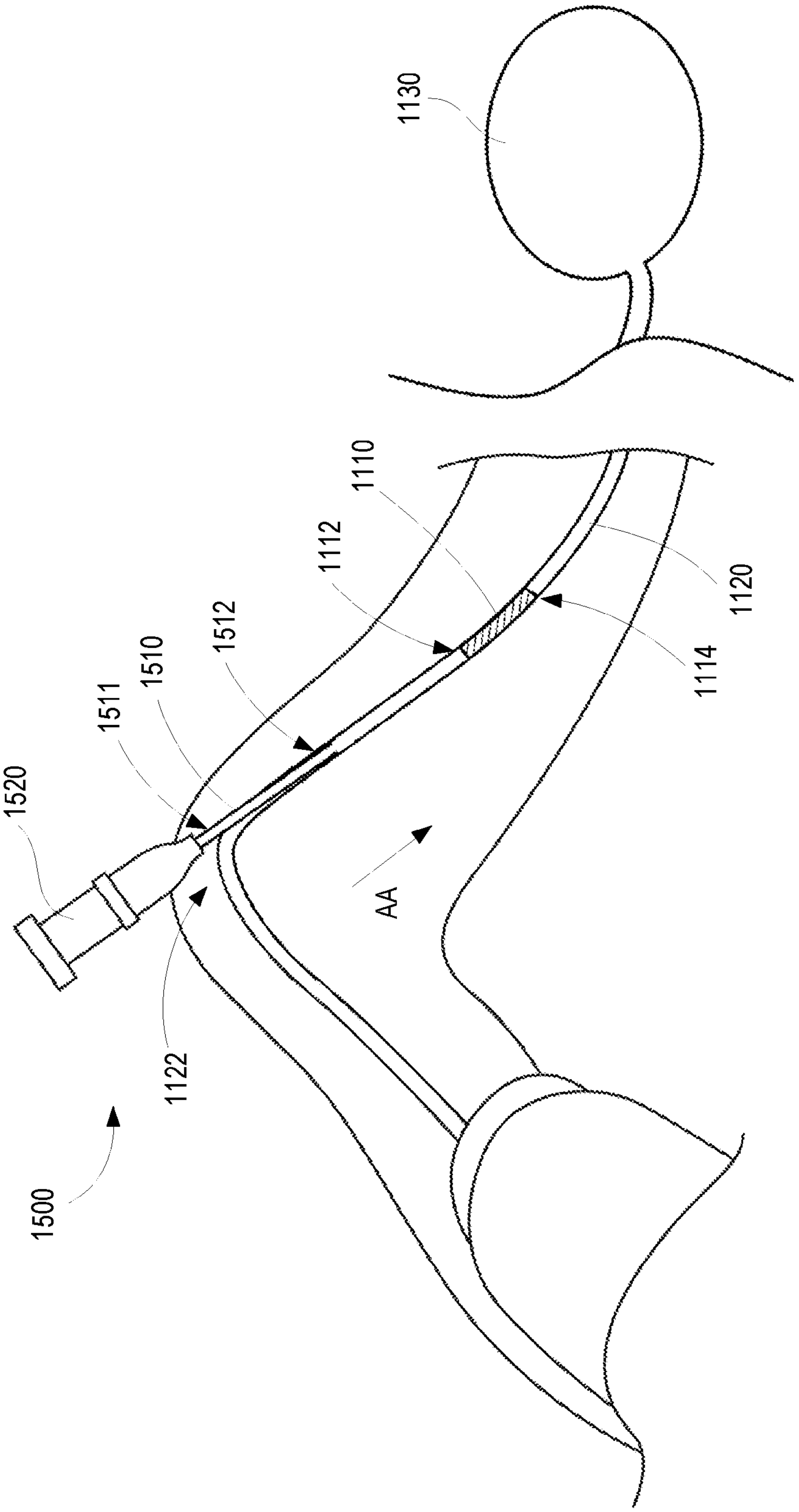
FIG. 1 is a schematic illustration of a delivery member inserted into a first body lumen occluded by a biomaterial implant according to an embodiment.

As generally described in related U.S. Pat. Nos. 11,253,391 and 11,318,040, each entitled "Systems and Methods for Delivering of Biomaterials," and in related International Patent Application No. PCT/US2021/032235 entitled "Biomaterial Compositions and Methods of Delivery," each of which is incorporated herein for all purposes, a biomaterial (e.g., a hydrogel) can be implanted into or onto a body lumen, or other cavity, space, tissue or organ of a body. A delivery apparatus is used to inject the formed (or partially formed) biomaterial. The biomaterial may be formed and extruded into a body lumen or formed directly in the body lumen. The biomaterial may continue to gel and/or cross-link in situ once injected or can be completely gelled or cross-linked by the time it exits the apparatus. In this regard, the delivery apparatus can facilitate the merging or mixing of the two or more different solutions into a single stream. In some embodiments, the selected body lumen is a vas deferens, and the biomaterial is delivered and implanted in the vas deferens to occlude the vas deferens and serve as contraception. In some embodiments, the selected body lumen is a fallopian tube, and the biomaterial is delivered and implanted in the fallopian tube to occlude it and serve as contraception. In some embodiments, the biomaterial includes a drug an is implanted into the selected body lumen to promote delivery of the drug.

In some embodiments, the biomaterial is a single-component hydrogel. However, in some embodiments, the biomaterial includes a first component and a second component that are each water-soluble components. The first component and the second component are capable of crosslinking to form the hydrogel. The hydrogel formed by crosslinking the first component and the second component can be at least 80 percent water. In some embodiments, the first component is characterized by having a first viscosity. The second component is characterized by a second viscosity, and the second viscosity is within 25 percent of the first viscosity. In some embodiments, the hydrogel formed by crosslinking the first component and the second component has a gelation time of less than 5 minutes. In some embodiments, the biomaterial has a cohesion (e.g., structural integrity) that is greater than the cohesion of a biological occlusion (e.g., a blood clot). Accordingly, removal of the biomaterial can require greater forces than those required to remove a biological occlusion.

In some embodiments, the conveying of the hydrogel out of the delivery apparatus includes conveying the hydrogel into or onto a body part, cavity, or lumen to at least partially occlude the body part or lumen. In some embodiments, the body part, cavity or lumen is one of an artery, vein, capillary, vessel, tissue, intra-organ space, lymphatic vessel, vas deferens, epididymis, fallopian tube, duct, bile duct, hepatic duct, cystic duct, pancreatic duct, parotid duct, organ, uterus, prostate, organ of a gastrointestinal tract or circulatory system or respiratory system or nervous system, subcutaneous space, intramuscular space, or interstitial space. In some embodiments, the hydrogel conveyed to the body lumen at least partially occludes the body lumen. In some embodiments, the hydrogel can additionally or alternatively provide contraceptive effect to a subject or induce azoospermia or infertility in a subject. In some embodiments, the conveying the hydrogel out of the delivery apparatus is performed in less than 30 seconds. In some embodiments, the conveying the hydrogel out of the delivery apparatus includes conveying between about 50 microliters to about 2.0 milliliters to a lumen, cavity, space, tissue or organ of a body. In some embodiments, the conveying the hydrogel out of the delivery apparatus includes conveying between about 50 microliters and about 250 microliters to a lumen, cavity, space, tissue, or organ of a body in between about 5 seconds and about 60 seconds. Thus, the methods of implant removal described herein can be performed to remove an implant from any of these body lumens.

Any of the methods of removal described herein can be performed to remove any of the biomaterials described herein. For example, any of the methods can be used to remove (or reverse implantation of) any of the hydrogels described herein. In some embodiments, the hydrogel is echogenic and the method includes identifying the hydrogel or a bolus of air via an image of the body lumen, such as by ultrasound. In some embodiments, the body lumen is one of an artery, vein, capillary, vessel, tissue, intra-organ space, lymphatic vessel, vas deferens, epididymis, fallopian tube, duct, bile duct, hepatic duct, cystic duct, pancreatic duct, parotid duct, organ, uterus, prostate, organ of a gastrointestinal tract or circulatory system or respiratory system or nervous system, subcutaneous space, intramuscular space, or interstitial space.

In some embodiments, the hydrogel is conveyed out of the exit opening of the delivery apparatus into a body lumen to at least partially occlude the body lumen. In some embodiments, the body lumen is one of an organ of a reproductive system. In some embodiments, the body lumen is one of a vas deferens or a fallopian tube. In some embodiments, the body lumen has an inner diameter of about 10.0 mm or less. For example, in some embodiments, the body lumen has an inner diameter of about 1.0 mm or less. In some embodiments, the body lumen is surrounded by smooth muscles.

In some embodiments, wherein the biomaterial is formed by combining at least two components, the first component and the second component can be any of the biomaterial components described herein. For example, in some embodiments, the first component and the second component can each be a water-soluble component (e.g., monomer, macromer, polymer, or the like) that is capable of crosslinking (e.g., with the other component) to form a hydrogel (as the delivered biomaterial product). In some embodiments, the first component and the second component are formulated such that the resulting hydrogel has a gelation time of less than 5 minutes. In other embodiments, the first component and the second component are formulated such that the resulting hydrogel has a gelation time of less than 2.0 minutes. In yet other embodiments, the first component and the second component are formulated such that the resulting hydrogel has a gelation time of less than 30 seconds. In some embodiments, the first component is at least one of a polyvinyl alcohol, alginate or modified alginate, chitosan or modified chitosan, polyethyleneimine, carboxymethyl cellulose, and/or polyethylene glycol terminated with one or more bioorthogonal functional group (e.g., amine, thiol, maleimide, azide, alkyne activated ester). The second component is at least one of a water or buffer, water or buffer with divalent cations such as calcium, a solution of reduced hyaluronic acid, a solution of polystyrene sulfonate, a solution of gelatin, and/or polyethylene glycol terminated with one or more functional groups (e.g., amine, thiol, maleimide, azide, activated ester, alkyne, alkene, tetrazine). In some embodiments, polyvinyl alcohol, alginate, chitosan, polyethyleneimine, carboxymethyl cellulose, polyethylene glycol terminated with functional groups, divalent cations, reduced hyaluronic acid, polystyrene sulfonate, or gelatin have a weight percent ranging from about 1 to 30% in solvent, such as about 2 to 10%, about 3 to 12%, about 4 to 15%, about 5 to 20%, about 6 to 25%, or about 7 to 28%, or any range in between any of these endpoints. In some embodiments, the polysaccharides may be modified with one or more functional groups, such as the same or different functional groups. For example, the functional groups may include one or more of alcohols, amines, thiols, carboxylic acids, carboxylic acid derivatives, carbonates, carbamates, carbamides, alkanes (n=2 to n=12), alkenes, alkynes, maleimides, sulfones, vinyl sulfones, and activated carboxylic acids. In some embodiments, the polysaccharides and proteins may range in molecular weight from about 10,000 to about 1,000,000 grams/mole, such as about 15,000 to about 900,000 grams/mole, about 20,000 to about 850,000, about 25,000 to about 800,000, about 30,000 to about 700,000, about 50,000 to about 600,000, about 75,000 to about 500,000, about 100,000 to about 400,000, about 200,000 to about 300,000, or about 225,000 to about 275,000. In some embodiments, the polyvinyl alcohol, polystyrene sulfonate, polyethyleneimine, and polyethylene glycol may be linear, Y-shaped, 3-arm, 4-arm, 6-arm, or 8-arm, or be hyperbranched, and range in molecular weight from about 1,000 to about 1,000,000 grams/mole such as about 1,500 to about 900,000 grams/mole, about 2,000 to about 850,000, about 2,500 to about 800,000, about 3,000 to about 700,000, about 5,000 to about 600,000, about 7,500 to about 500,000, about 10,000 to about 450,000, about 15,000 to about 50,000, about 100,000 to about 400,000, about 200,000 to about 300,000, or about 225,000 to about 275,000 grams/mole, or any range in between any of these endpoints. The hydrogel can be any of the hydrogels described herein and can have any of the characteristics as indicated herein. For example, in some embodiments, the formed hydrogel can be at least 80 percent water, such as 92%, 93%, 94%, 95%, 96%, 97%, 98%, or 99%, or any range in between. In other embodiments, the formed hydrogel can be >50% water.

In some embodiments, the dissolving solution for the polymer component(s) may be aqueous buffers, including any one or more of phosphate, citrate, acetate, histidine, lactate, tromethamine, gluconate, aspartate, glutamate, tartrate, succinate, malic acid, fumaric acid, alpha-ketoglutaric, and/or carbonate. Specific solvents/buffers can include: 1) acetic acid and sodium acetate (AA), 2) citric acid and sodium citrate (CP), 3) citric acid and phosphate buffer (CP), and 4) phosphate buffer (PB). Non-aqueous solvents include: dimethyl isosorbide, glycofurol 75, PEG 200, diglyme, tetrahydrofurfuryl alcohol, ethanol, acetone, solketal, glycerol formal, dimethyl sulfoxide (DMSO), propylene glycol, ethyl lactate, N-methyl-2-pyrrolidone, dimethylacetamide, methanol, isopropanol, 1,4-butanediol, ethyl acetate, toluene, acetonitrile. The molarity of the solutions/solvents/buffers can range for example from about 0.01 M to about 0.15 M to about 0.3 M, such as about 0.12 M to about 0.17 M to about 0.19 M, or any range in between any of these endpoints. In some embodiments, the solution can include about a 0.2 M citric acid buffer and can be formulated to have a solution pH of between 4.0 and 6.0. In some embodiments, the pH of the solution can be between 4.0 and 5.25. In some embodiments, the pH of the solution can be about 4.0. In other embodiments, the pH of the solution can be about 5.25. In yet other embodiments, the pH of the solution can be between about 4.5 and about 8 such as a pH of about 5-7, or about 4.5-6.

The term "about" when used in connection with a referenced numeric indication means the referenced numeric indication plus or minus up to 10% of that referenced numeric indication. For example, "about 100" means from 90 to 110.

The term "substantially" when used in connection with, for example, a geometric relationship, a numerical value, amount, and/or a range, such as with respect to a concentration, a volume, and/or movement/rate/speed, is intended to convey that the geometric relationship (or the structures described thereby), the number, and/or the range so defined is nominally the recited geometric relationship, number, and/or range. For example, two structures described herein as being "substantially parallel" is intended to convey that, although a parallel geometric relationship is desirable, some non-parallelism can occur in a "substantially parallel" arrangement. By way of another example, a structure defining a volume that is "substantially 0.50 milliliters (mL)" is intended to convey that, while the recited volume is desirable, some tolerances can occur when the volume is "substantially" the recited volume (e.g., 0.50 mL). Such tolerances can result from manufacturing tolerances, measurement tolerances, and/or other practical considerations (such as, for example, minute imperfections, age of a structure so defined, a pressure or a force exerted within a system, and/or the like). As described above, a suitable tolerance can be, for example, of ±10% of the stated geometric construction, numerical value, and/or range.

As used herein, the term "biomaterial component" (also referred to as "component") includes any substance that is used in connection with any of the systems or delivery devices described herein to form a delivered biomaterial product. For example, a component can include a small molecule, catalyst, peptide, protein, enzyme, nucleotide (or derivatives of), short chains of nucleotides (or derivatives of), long chains of nucleotides (or derivatives of), monosaccharides (or derivatives of), disaccharides (or derivatives of), trisaccharides (or derivatives of), oligo saccharides (or derivatives of), polysaccharides (or derivatives of), monomer, oligomer, macromer, or polymer that can be cross-linked with another component to form a delivered product (e.g., hydrogel). A component can include a mixture or solution of one or more constituents (e.g., a polymer and a solvent). A component can include such constituents regardless of their state of matter (e.g., solid, liquid or gas). A component can include both active constituents and inert constituents. For example, in some embodiments, a component can include certain polymers that can form a delivered product, as well as a medicament or other active ingredient. By way of another example, in some embodiments, a component can include drugs, including but not limited to, small molecule drugs and biologics. In other embodiments, a component can include certain constituents to impart desired properties to the delivered product, including constituents that facilitate the delivered product being echogenic, radiopaque, radiolucent, or the like.

The term "biomaterial product," "delivered biomaterial product," or "delivered product" includes any substance that is delivered by any of the systems or delivery devices described herein. For example, a delivered product can be a biomaterial that is formed from multiple biomaterial components and delivered with any of the delivery systems described herein and then delivered to target locations. Thus, a delivered product can be the implant or structure that is formed with the system by multiple biomaterial components that react together or assemble into higher order structures via covalent and/or non-covalent bonds or interactions, and that is delivered by the system. In certain situations, the biomaterial can be delivered by the system in a fully formed state to a target location. Although a delivered product can be considered fully formed (i.e., the chemical reactions between the biomaterial components are completed), it can still undergo certain changes (e.g., in vivo changes) after delivery. For example, a delivered biomaterial product can continue to absorb water and/or swell and/or can expel impurities. In some embodiments, a delivered biomaterial product can be a hydrogel that is formed by crosslinking of two or more biomaterial components. The term "hydrogel" can refer to any water-swollen (majority, >50%, of material mass is water), and cross-linked polymeric network produced by the reaction of one or more components (e.g., polymers, monomers) and/or a polymeric material that exhibits the ability to swell and retain a significant fraction of water within its structure, but will not dissolve in water.

As used herein, the term "set" can refer to multiple features or a singular feature with multiple parts. For example, when referring to set of walls, the set of walls can be considered as one wall with multiple portions, or the set of walls can be considered as multiple, distinct walls. Thus, a monolithically-constructed item can include a set of walls. Such a set of walls can include, for example, multiple portions that are either continuous or discontinuous from each other. A set of walls can also be fabricated from multiple items that are produced separately and are later joined together (e.g., via a weld, an adhesive, or any suitable method).

The term "gelation" refers to the transition of the hydrogel components from a soluble polymer of finite branches to a viscoelastic material. Similarly stated, "gelation" refers to the condition where the gel forms and after the components are combined. Thus, the gelation time refers to the time that it takes for the resulting hydrogel to substantially reach equilibrium.

The term "downstream" refers to the direction of an intended or normal flow of fluid within a body lumen or channel. The term "upstream" refers to the direction opposite of the downstream direction, or opposite the direction of the intended or normal flow of fluid within a body lumen or channel. For example, the downstream direction within the vas deferens is the direction from the testes towards the penile urethra. The downstream direction within the fallopian tubes is from the infundibulum to the uterus.

As used herein, the terms "proximal" and "distal" refer to direction closer to and away from, operator executing the methods described herein. Thus, for example, the proximal end portion of a delivery member is the portion of the delivery member that is maintained external to the body lumen, while the distal end portion is positioned within the body lumen. Similarly, the term "proximal" and refer to the upstream direction, while the term "distal" can refer to the downstream direction.

As depicted in FIGS. 1-9, the systems and methods described herein can be employed to remove implant 1110 (e.g., a hydrogel implant) from a body lumen (e.g., a vas deferens) without damaging the body lumen. The body lumen can, for example, have a maximal inner diameter in a range of 0.75 mm to 2.0 mm. The observed flow of a contrast media introduced upstream of the implant 1110 can be indicative of the integrity, and/or location of the implant 1110. In some embodiments, removal (e.g., disruption) of the implant 1110 as described herein results in at least one of A) a total sperm motility of sperm passing through the vas deferens after removal of the implant being substantially similar a total sperm motility before placing of the implant in the vas deferens, B) a total sperm concentration passing through the vas deferens after the disruption of the implant being substantially similar to a total sperm concentration before placing of the implant in the vas deferens, C) an ejaculate volume passing through the vas deferens after the disruption of the implant to be substantially similar to the ejaculate volume before placing of the implant in the vas deferens, or D) a forward progression of sperm through the vas deferens after the disruption of the implant being substantially similar to a forward progression of sperm before placing of the implant in the vas deferens. However, in some embodiments, the new implant can be positioned within the body lumen following completion of the removal procedure. For example, the removal and reimplantation procedures can be used to replace an implant that is approaching a life-cycle limit to maintain the occlusion of the body lumen.

In some embodiments, removal of the implant 1110 as described herein results in at least one of: A) a total sperm motility of sperm passing through the vas deferens at the implant location after the disruption of the implant being at least 30% to 70% of a total sperm motility of the sperm passing through the vas deferens at a location upstream from the implant location, B) a total sperm concentration passing through the vas deferens at the implant location after the disruption of the implant being at least 30% to 70% of a total sperm concentration passing through the vas deferens at the location upstream from the implant location, or C) an ejaculate volume passing through the vas deferens at the implant location after the disruption of the implant being at least 30% to 70% of an ejaculate volume before passing through the vas deferens at the location upstream from the implant location. In some embodiments, removal of the implant 1110 as described herein results in a total sperm motility of sperm passing through the vas deferens at the implant location after the disruption of the implant being at least about 25 micrometers per second. In some embodiments, removal of the implant 1110 as described herein results in an effective diameter of an inner lumen of the vas deferens at the implant location after the disruption of the implant being substantially similar to the effective diameter of an inner lumen of the vas deferens at a location directly upstream from the implant location. In some embodiments, removal of the implant 1110 as described herein results in restoration of flow through the vas deferens at the implant location. In some embodiments, removal of the implant 1110 includes a flush solution 1900 (FIG. 8) being conveyed through the implant location of the vas deferens with a force of less than or equal to about 44.48 N (10 lbF). The flush solution can have a volume of at least about 0.01 mL to about 10 mL that is conveyed into and through the vas deferens.

In some embodiments, "substantially similar" or "substantially the same" in the context of total sperm motility, total sperm concentration, ejaculate volume, or forward progression of sperm, or inner diameter of the vas deferens, includes differences in measurements taken before and after removal or disruption of the implant of up to about 50%, such as a difference of about 5-10%, or a difference of about 10-20%, or a difference of about 20-30%, or a difference of about 30-40%, or a difference of about 40-50%, or any range between any of these endpoints. In embodiments, "substantially similar" includes an increase in any amount from before to after in any one or more of total sperm motility, total sperm concentration, ejaculate volume, or forward progression of sperm. In some embodiments, a test for whether after removal or disruption of an implant the total sperm motility, total sperm concentration, ejaculate volume, or forward progression of sperm is substantially the same as before installation of the implant can be performed in vitro with the implant and removal device, such as in a simulated body lumen, including polyethylene tubing. Such tests can also be performed in other subjects, such as in mice, dogs or rabbits. In some embodiments, "substantially similar" or "substantially the same" in the context of effective diameters of the inner lumen of the vas deferens at the location of the implant and at the location directly upstream of the implant includes a difference of up to about 25%. In some embodiments, the distance from the implant location to the location directly upstream of the implant is about 1 cm. It is noted that depending on the patient, the effective diameter of the inner lumen of the vas deferens at the location of the implant may compress down towards to an original effective diameter (i.e., prior to the presence of the implant) over a period of days, weeks, months, or years after the disruption and/or removal of the implant. For some patients, the vas at the implant location may remain dilated beyond the original effective diameter.

In some embodiments, the total sperm motility of sperm passing through the vas deferens after removal of the implant 1110 is at least about 30% to 70% (e.g., not more than a about 30-50% reduction or difference) the total sperm motility before placing of the implant in the vas deferens. In some embodiments, the total sperm motility of sperm passing through the vas deferens after removal of the implant 1110 is at least about 60% to 70% (e.g., not more than about 30-40% reduction or difference) the total sperm motility before placing of the implant in the vas deferens. In some embodiments, the total sperm motility of sperm passing through the vas deferens after removal of the implant 1110 is at least about 70% to 80% (e.g., not more than about 20-30% reduction or difference) the total sperm motility before placing of the implant in the vas deferens. In some embodiments, the total sperm concentration passing through the vas deferens after removal of the implant 1110 is at least about 85% to 95% (e.g., not more than about 5-15% reduction or difference) the total sperm concentration before placing of the implant in the vas deferens. In some embodiments, the removal of the implant 1110 results in a post-implant motility of sperm passing through the vas deferens after removal of the implant 1110 that is sufficient to travel through a female reproductive tract and to fertilize an egg. In some embodiments, proteins and organelle (e.g., acrosome) of sperm passing through the vas deferens after the removal of the implant 1110 remain unaltered in substantially the same fashion as proteins and organelle of sperm passing through the vas deferens prior to the implant 1110.

FIG. 1 shows a schematic illustration of a delivery member 1500 being inserted into a first body lumen 1120 including an implant 1110 that occludes the first body lumen 1120. The insertion of the delivery member 1500 establishes an entry point 1122 into the first body lumen 1120. The delivery member 1500 includes a catheter 1510 and a hub portion 1520. The catheter 1510 includes a proximal end portion 1511 and a distal end portion 1512. The proximal end portion 1511 is coupled to the hub portion 1520. The distal end portion 1512 of the catheter 1510 is inserted into a first body lumen 1120 upstream of the implant 1110 and extending in a downstream direction of the first body lumen 1120, as shown by the arrow AA. In some embodiments, the distal end portion 1512 is inserted into the first body lumen 1120 upstream of the implant 1110 such that the implant 1110, fragments of the implant 1110, and/or a remnant 1116 (FIG. 8) can be conveyed downstream towards a second body lumen 1130 and a natural outlet, such as a urinary tract, of a patient. For example, in some embodiments, the distal end portion 1512 is inserted into a vas deferens upstream of the implant 1110 and a force exerted on the implant 1110 causes at least a portion of the implant 1110 to move from the vas deferens to the bladder or urethra. From the bladder, the portion of the implant 1110 can exit the body via the urethra. In some embodiments, the delivery member 1500 is an angiocatheter.

Figure 9:
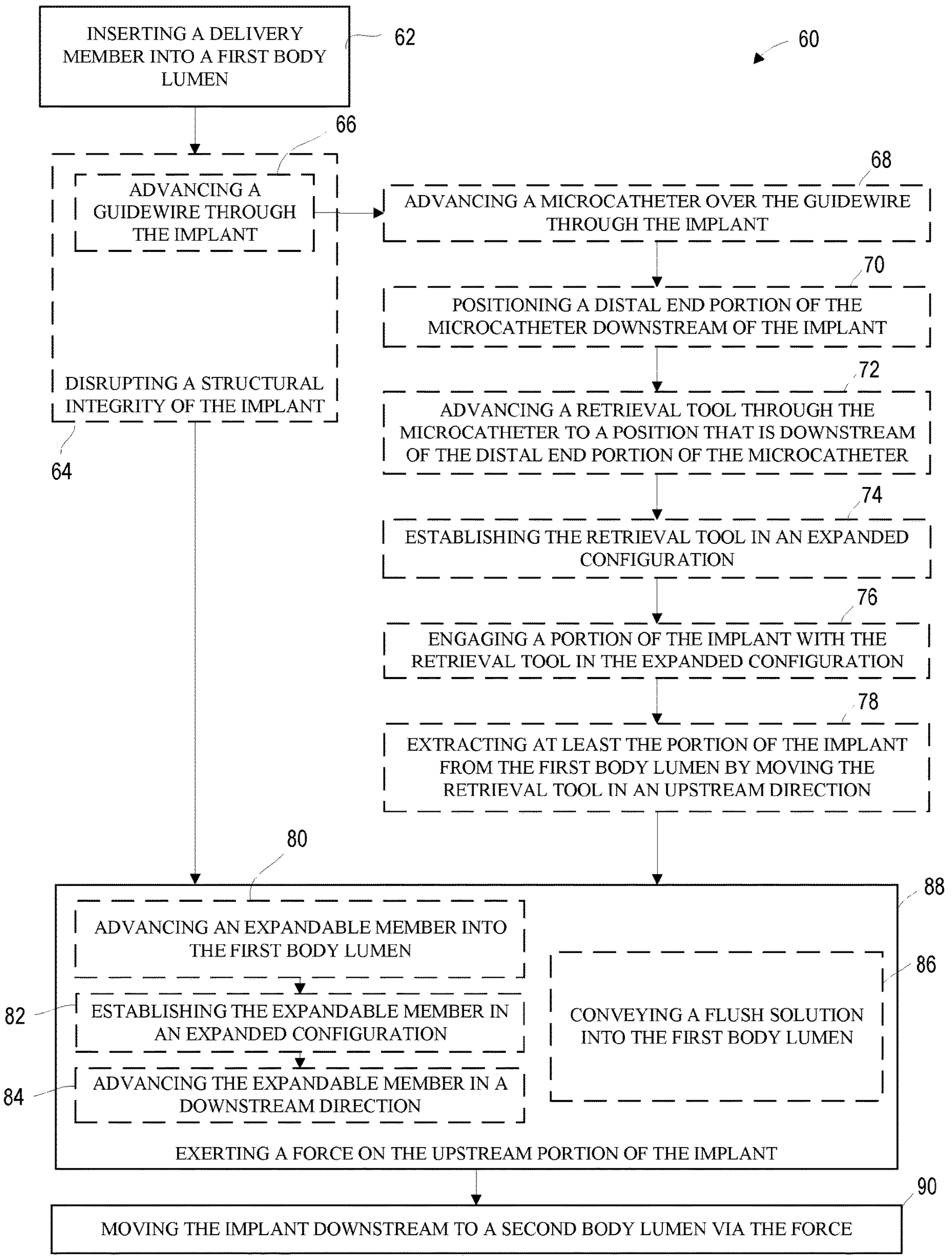
FIG. 9 is a flow chart of a method of removing a biomaterial implant from a first body lumen according to an embodiment.

In some embodiments, the delivery member 1500 can facilitate implementation of the method 60 to remove an implant 1110 from a body lumen. FIG. 9 is a flow chart of the method 60 for removing the implant 1110 from a body lumen. In some embodiments, the body lumen can be a vas deferens having an internal diameter that is less than 1 mm (e.g., 0.8 mm). At step 62, the delivery member 1500 is inserted into the first body lumen 1120 and placed in fluid communication with an upstream portion 1112 of the implant 1110. For example, a vas deferens (e.g., the first body lumen 1120) that is occluded by the implant 1110 is cannulated using an over-the-needle catheter upstream to the implantation site. In some embodiments, a force is exerted at step 88 on the upstream portion 1112 of the implant 1110. The force exerted at step 88 is exerted in a downstream direction (e.g., the direction from the testes towards the penile urethra). At step 90, the implant 1110 is moved downstream to a second body lumen 1130 (e.g., a bladder or other portion of the urinary tract) by the force exerted at step 88 in the downstream direction (e.g., in the direction indicated by arrow AA in FIG. 1). The downstream movement of the implant 1110 is facilitated by an absence of a basket, filter, or other capture structure positioned downstream of the implant 1110 (e.g., between a downstream portion 1114 of the implant 1110 and the second body lumen 1130). It should be appreciated that in some embodiments, steps 88 and 90 can be executed in an upstream direction.

As depicted at step 64, in some embodiments, a structural integrity of the implant 1110 is optionally disrupted prior to exerting the force on the upstream portion 1112 at step 88. In other words, the cohesion of the implant 1110 can be disrupted to facilitate removal of the implant 1110.

In some embodiments, the structural integrity of the implant 1110 can, for example, be chemically disrupted. For example, in some embodiments, the implant includes an inert, non-biologic material. In some embodiments, the implant can be a hydrogel cross-linked in-situ within the vas deferens. In some embodiments, the implant can be a co-polymer injected in dimethyl sulfoxide. The implant can be a cross-linked hydrogel formed from a first component and a second component. The first component can include at least one of a polyvinyl alcohol, alginate or modified alginate, chitosan or modified chitosan, polyethyleneimine, carboxymethyl cellulose, or polyethylene glycol terminated with a functional group such as a bioorthogonal functional group. The second component can include at least one of a water or buffer, water or buffer with divalent cations such as calcium, a solution of reduced hyaluronic acid, a solution of polystyrene sulfonate, a solution of gelatin, and/or polyethylene glycol terminated with a functional group, such as a bioorthogonal functional group. In some embodiments, the first component can include a multi-arm polyethylene glycol terminated with thiol, and the second component can include a multi-arm polyethylene glycol terminated with a maleimide. In some embodiments, the multi-arm polyethylene glycol terminated with thiol and/or the multi-arm polyethylene glycol terminated with a maleimide have a weight percent ranging from about 1 to about 30% in solvent. In some embodiments, the multi-arm polyethylene glycol may be linear, Y-shaped, 3-arm, 4-arm, 6-arm, or 8-arm, or hyperbranched. In some embodiments, the first component and the second component are formulated to have a pH less than about 5.25. Accordingly, exposing the implant 1110 to a solvent of sufficient concentration for a specified time interval can chemically disrupt the cohesion of the implant. Similarly, introducing a brine solution (e.g., a solution including at least 2.5% dissolved NaCl) to the first body lumen 1120 can chemically disrupt the structural integrity of the implant 1110. For example, the brine solution can cause the implant 1110 to shrink thereby decreasing the diameter of the implant 1110 and facilitating the removal thereof.

In some embodiments, the structural integrity of the implant 1110 can be mechanically disrupted by advancing a tool member at least partially through the implant 1110. The tool member can include a guidewire 1600 (FIG. 2), a microcatheter 1550 (FIG. 3), a retrieval tool 1700 (FIGS. 4-5), an expandable member 1800 (FIGS. 6-7), an ablation device (not shown), and/or other tool member having a rigidity that is greater than the cohesion of the implant 1110. In additional embodiments, the tool member can be a thermal and/or a wave/vibrational energy implement configured to mechanically disrupt the cohesion.

As described in International Patent Application No. PCT/US2021/034562 entitled "Systems and Methods for Removing Biomaterial Implants," which is incorporated herein for all purposes, in some embodiments the tool member, such as an ablation device, is inserted into the first body lumen via the delivery member 1500. The tool member can include a control unit, a motor, a driveshaft, and an engagement member. The control unit can be operatively connected to the motor to control one or more of a rotational speed, rotational torque, or rotational direction of the motor. In some embodiments, the control unit can receive inputs from an operator to start or stop the motor, to control a rotational direction of the motor, and/or to control the speed of the motor. The engagement member can include a working surface configured to ablate, cut, mill, and/or grind a material that the working surface comes into contact with. In some embodiments, the engagement member includes an abrasive tip, a cutting tip, a milling tip, a grinding tip, a coring tip, and/or a boring tip. In some embodiments, the engagement member can be a diamond coated tip and can be formed from one or more of diamond, gold, aluminum, steel, titanium nitride, tungsten carbide, boron carbide, or silica material.

Figure 2:
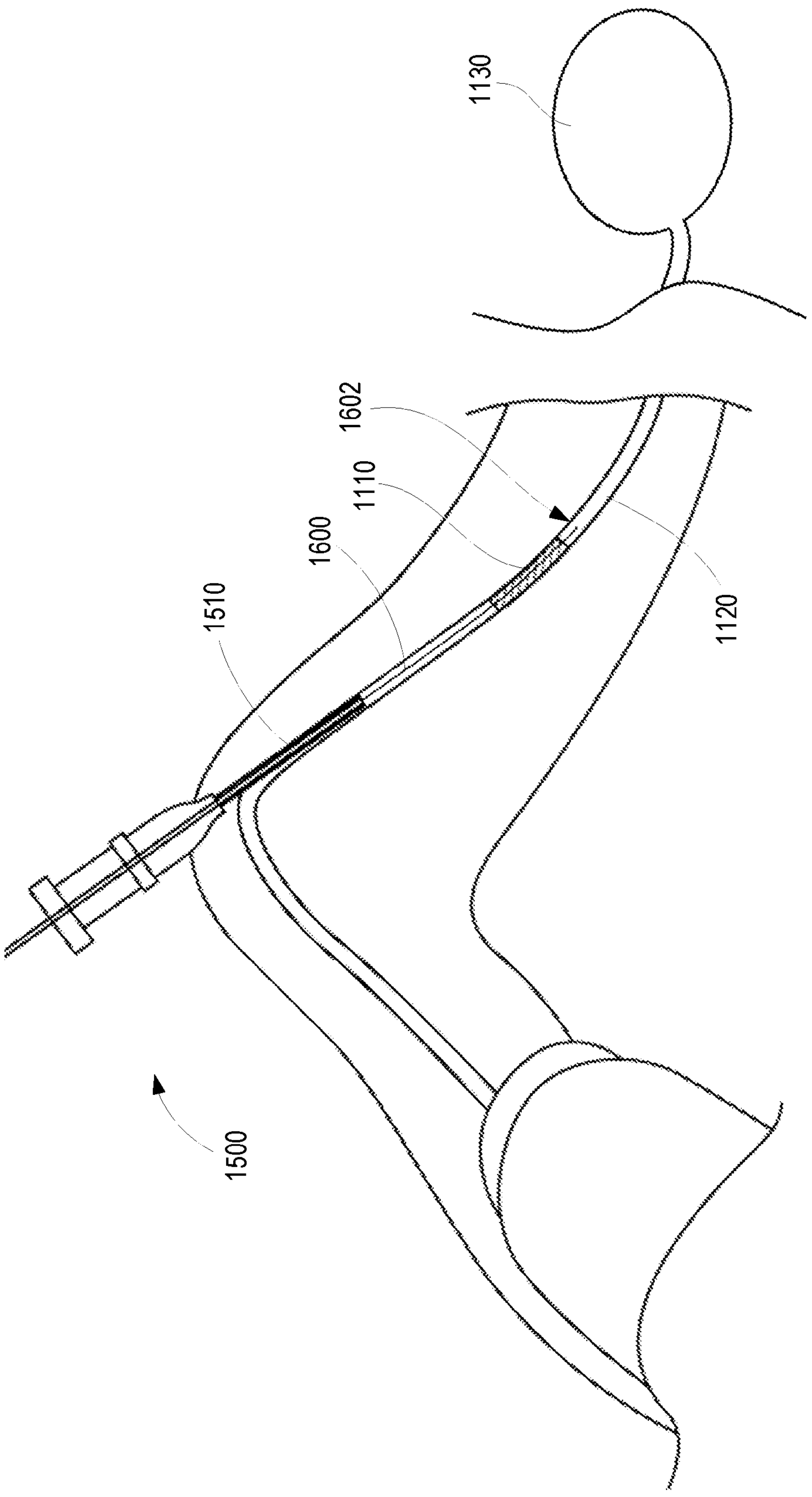
FIG. 2 is a schematic illustration of a guidewire inserted into the first body lumen and through the biomaterial implant according to an embodiment.

As depicted in FIG. 2, in some embodiments, disrupting the structural integrity of the implant 1110 optionally includes advancing a guidewire 1600 through the delivery member 1500 and into the first body lumen 1120. In this manner, the disruption can occur within or near a central portion of the implant 1110, thus minimizing the likelihood that a tool may be deflected towards the wall of the first body lumen 1120. Thus, this method can reduce the likelihood of perforation of the wall of the first body lumen 1120. At step 66, the guidewire 1600 can then be advanced through the implant 1110. Said another way, the guidewire 1600 can be inserted through the over-the-needle catheter into the vas deferens and advanced to place a distal end portion 1602 of the guidewire 1600 at a location that is downstream of the implant 1110. In some embodiments, the guidewire 1600 as a diameter of at least 170 μm and less than or equal to 355 μm. In some embodiments, the guidewire 1600 can be formed from any of stainless-steel, nitinol, platinum (all alloys), palladium, tungsten and/or combinations thereof. In some embodiments, the guidewire 1600 and be a composite structure having a core surrounded by a coil. For example, the guidewire 1600 can be a neurovascular guidewire. In some embodiments, upon the positioning of the distal end portion 1602 of the guidewire 1600 at a location that is downstream of the implant 1110, the delivery member 1500 can be removed.

Figure 3:
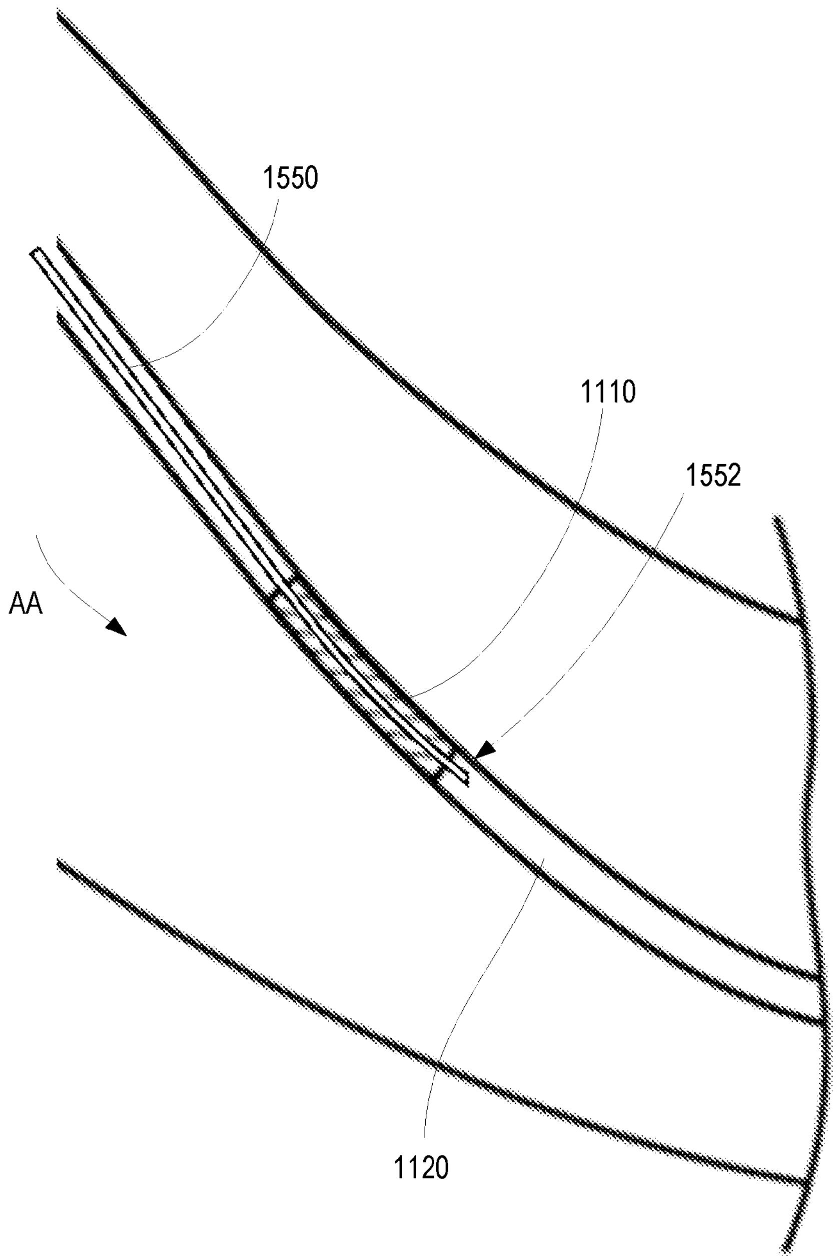
FIG. 3 is a schematic illustration of a microcatheter advanced through the biomaterial implant within the first body lumen according to an embodiment.

As depicted at step 68, in some embodiments, a microcatheter 1550 (e.g., a guide lumen) can be advanced over the guidewire 1600. As depicted in FIG. 3, the microcatheter 1550 can be advanced through the implant 1110. At step 70, a distal end portion 1552 of the microcatheter 1550 can be positioned downstream of the implant 1110. In some embodiments, the microcatheter 1550 has an outer diameter that is less than 1 mm (e.g., less than or equal to 0.9 mm and greater than or equal to 0.7 mm) to facilitate entry into a vas deferens (e.g., a body lumen having an inner diameter of 1 mm or less). The microcatheter 1550 can include an integrated steerable or angled tip and a lubricious coating. With the distal end portion 1552 of the microcatheter 1550 positioned downstream of the implant 1110, the guidewire 1600 can be removed. In some embodiments the position of the delivery member 1500 and/or the guidewire 1600 can be observed via medical imaging techniques (e.g., fluoroscopy or ultrasound).

Figure 4:
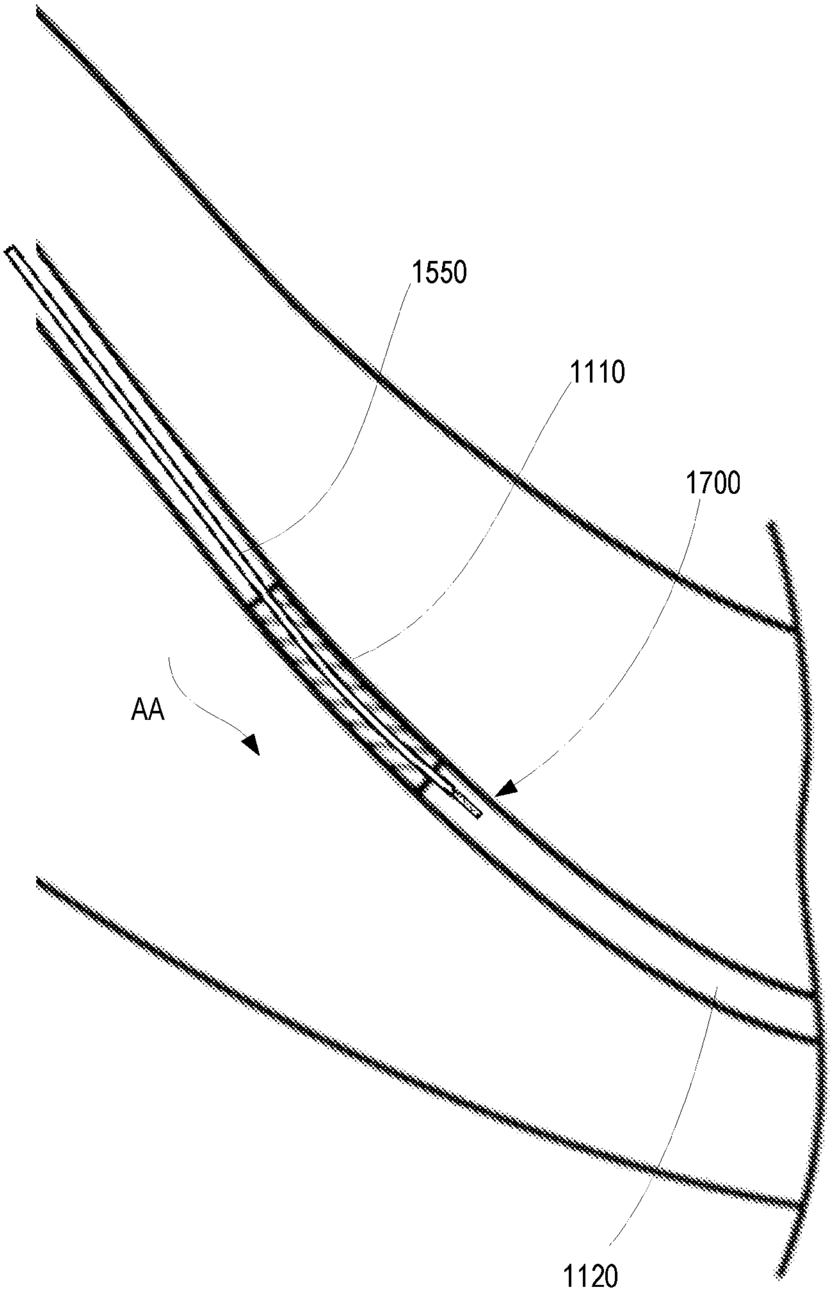
FIG. 4 is a schematic illustration of a retrieval tool in a collapsed configuration positioned downstream of a distal end portion of the microcatheter according to an embodiment.
Figure 5:
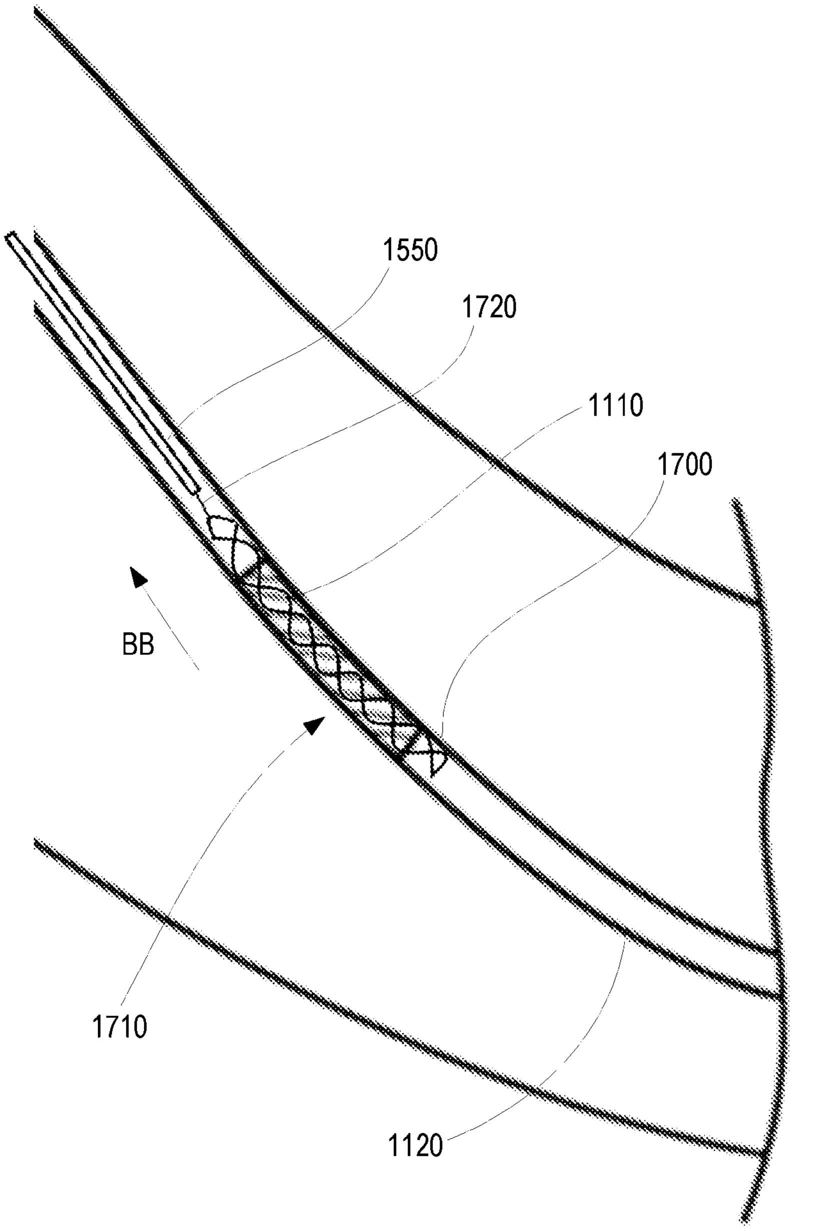
FIG. 5 is a schematic illustration of the retrieval tool of FIG. 4 in an expanded configuration according to an embodiment.

Referring now to FIGS. 4, 5, and 9, at step 72 a retrieval tool 1700 can be advanced through the microcatheter 1550. A portion of the retrieval tool 1700 can be positioned downstream of the distal end portion 1552 of the microcatheter 1550 as depicted in FIG. 4. The retrieval tool 1700 can have a collapsed configuration (e.g., FIG. 4) and an expanded configuration (e.g., FIG. 5). The retrieval tool 1700 can, for example, be a stent retriever, a balloon catheter, or other similar tool configured for neurovascular procedures (e.g., a thrombectomy). The stent retriever is a generally cylindrical apparatus that has an expanding stent portion 1710 coupled to a wire 1720. The expanding stent portion 1710 can include a plurality of interwoven elements (e.g., wires) configured to entangle an obstruction within the body lumen. In some embodiments, the expanding stent portion 1710 can include at least one wire in a spiral configuration. The expanding stent portion 1710 can be a self-expanding stent portion configured to transition from a collapsed configuration within a microcatheter to an expanded configuration, which has a greater diameter than the inner diameter of the microcatheter, when freed from the microcatheter. However, in some embodiments, the expanding stent portion 1710 can be expanded via an applied force (e.g., in response to the inflation of a balloon positioned radially inward of the expanding stent portion). The retrieval tool 1700 can for example, be configured for thrombosis removal from a body lumen having an internal diameter of 1 mm or less.

As depicted at step 74, the retrieval tool 1700 is transitioned to an expanded configuration as depicted in FIG. 5. For example, with at least a portion of the retrieval tool 1700 positioned downstream of the distal end portion 1552 of the microcatheter 1550, the microcatheter 1550 can be retracted (e.g., withdrawn in the upstream direction) to free the self-expanding stent portion 1710 of the retrieval tool 1700. The freeing of the self-expanding stent portion 1710 facilitates the transition of the retrieval tool 1700 from the collapsed configuration to the expanded configuration. With the retrieval tool 1700 in the expanded configuration, a portion of the implant 1110 can be engaged with the retrieval tool 1700 at step 76. Engagement of the portion of the implant 1110 with the retrieval tool 1700 can include an entanglement of at least a portion of the implant 1110 with the retrieval tool 1700. With at least a portion of the implant 1110 engaged by the retrieval tool 1700, the retrieval tool 1700 can be moved in upstream direction, as indicated by arrow BB. The upstream movement of the retrieval tool 1700 can be continued until the retrieval tool 1700 and the entangled portion of the implant 1110 is extracted from the entry point 1122. In some embodiments, the steps 68-78 and be repeated as necessary to remove additional portions of the implant 1110. However, in some embodiments, step 78 is followed by step 88 wherein the force is exerted on a remaining upstream portion of the implant 1110.

Figure 6:
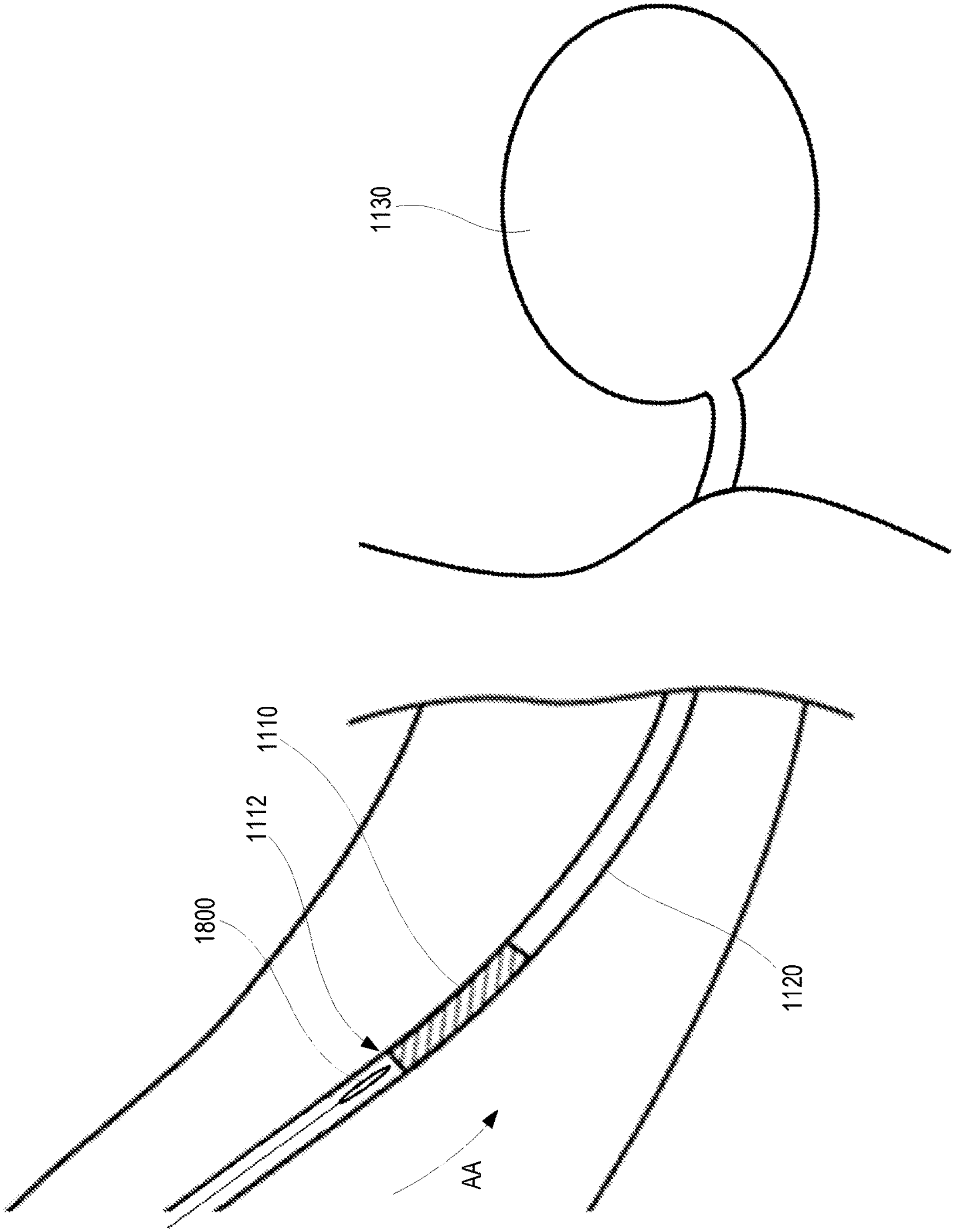
FIG. 6 is a schematic illustration of an expandable member positioned within the first body lumen according to an embodiment.
Figure 7:
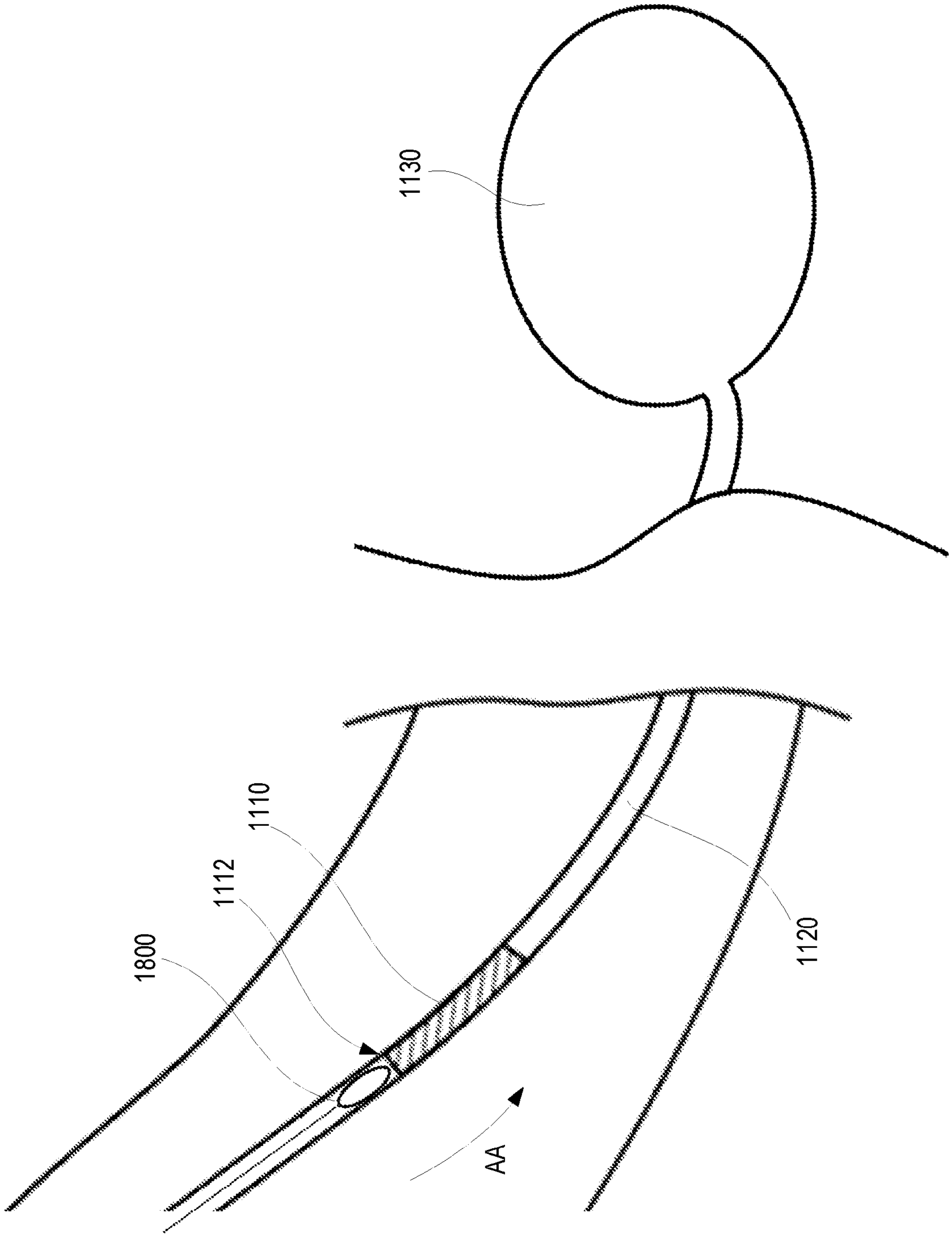
FIG. 7 is a schematic illustration of the expandable member of FIG. 5 in an expanded configuration according to an embodiment.

Referring now to FIGS. 6, 7, and 9, in some embodiments exerting the force on the upstream portion 1112 of the implant can include exerting a mechanical force via an expandable member 1800. As depicted at step 80, an expandable member 1800 can be advanced into the first body lumen 1120 in a collapsed configuration (e.g., FIG. 6). The expandable member 1800 can then be transitioned, at step 82, to an expanded configuration (e.g., FIG. 7). In the expanded configuration, the expandable member 1800 can have an outer diameter that occludes the first body lumen 1120. As depicted at step 84, the expandable member 1800, in the expanded configuration, can be advanced in the downstream direction to exert the force on the upstream portion 1112 of the implant 1110. The expandable member 1800 can continue to exert the force on the upstream portion 1112 to cause the implant 1110 to move downstream and into the second body lumen 1130.

In some embodiments, the expandable member 1800 can be a balloon catheter. The balloon catheter can be advanced over the guidewire 1600 in a deflated (e.g., collapsed) configuration until the balloon catheter is within the occluded vas deferens (e.g., the first body lumen 1120). The balloon catheter can then be inflated and advanced downstream into contact with the implant 1110. The balloon catheter can then be employed to drive the implant downstream and towards the bladder or the urethra (e.g., the second body lumen 1130). It should be appreciated that following the employment of the retrieval tool 1700, the guidewire 1600 can be reinserted into the first body lumen 1120 to facilitate the employment of the balloon catheter to drive a remaining portion (e.g., remnant 1116) of the implant 1110 from the vas deferens and towards the urethra. It should be appreciated that each of the methods and procedures disclosed herein can be accomplished after an incision (e.g., an access point) is made into the first body lumen (e.g., the vas deferens) and that the incision can be sutured after the removal procedure is complete.

Figure 8:
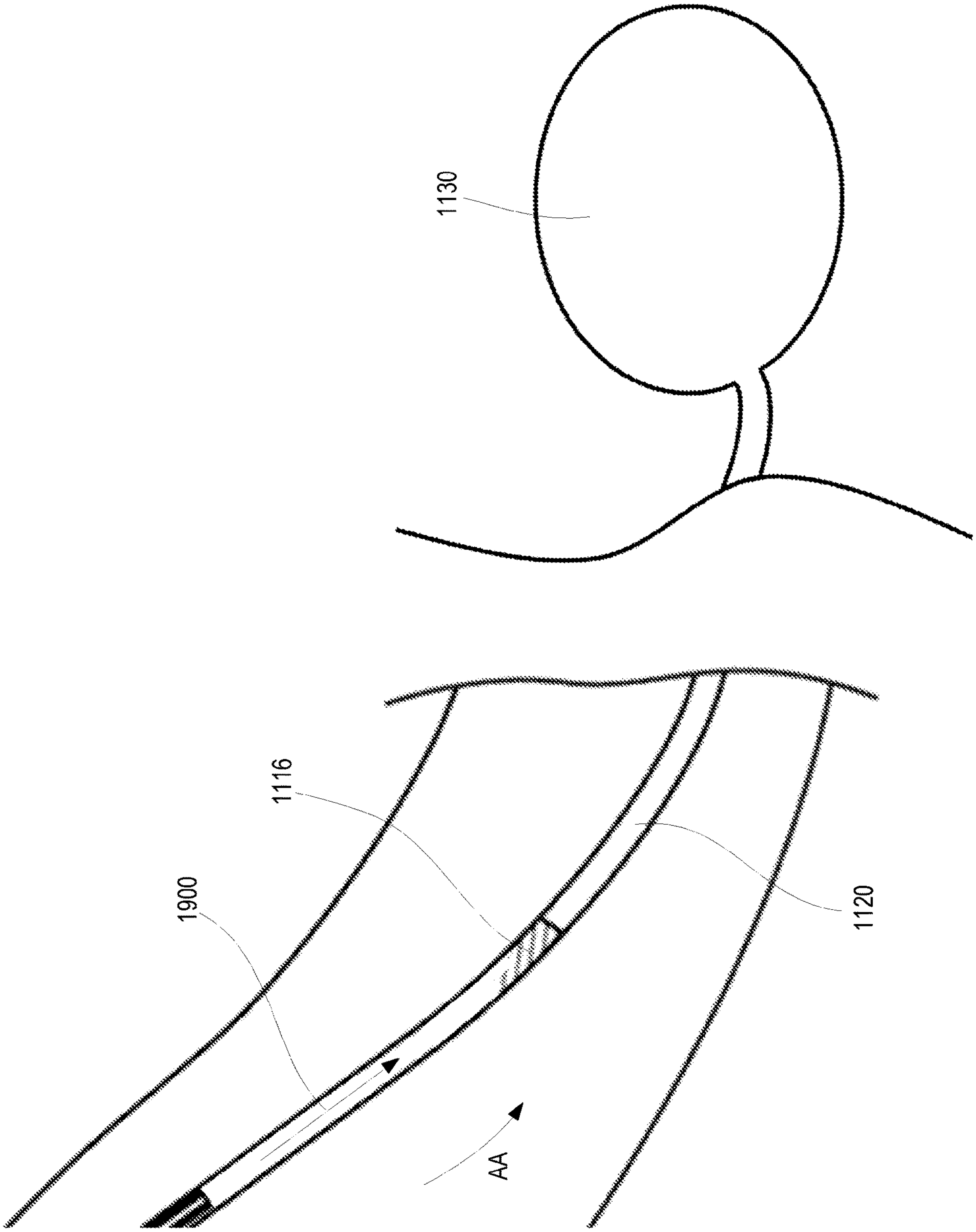
FIG. 8 is a schematic illustration of a remnant of the biomaterial implant within the first body lumen according to an embodiment.

Referring now to FIGS. 8 and 9, in some embodiments exerting the force on the upstream portion of the implant can include, at step 86, conveying a flush solution 1900 into the first body lumen 1120. The flush solution 1900 can convey the remnant 1116 (e.g., at least one fragment) of the implant 1110 downstream towards the second body lumen 1130. For example, in some embodiments, steps 66-78 can be employed to remove a substantial portion of the implant 1110. However, this may leave the remnant 1116 within the first body lumen 1120, which can impact flow through the first body lumen 1120. Accordingly, a flushing solution 1900 can be utilized to remove any obstructions to the flow through the first body lumen 1120. Similarly, in some embodiments, the flush solution 1900 can be introduced following the execution of steps 80-84 to remove the remnant 1116 from the first body lumen 1120. Additionally, in some embodiments, the flush solution 1900 can be introduced following any of the procedures described herein. Further, in some embodiments, the flush solution 1900 can be employed to exert the force on the upstream portion 1112 of the implant 1110, in accordance with step 88, in lieu of a mechanical engagement of the implant 1110, to move the implant 1110 downstream towards the second body lumen 1130. In still further embodiments, the flush solution 1900 can be employed to exert the force on the upstream portion 1112 of the implant 1110 in lieu of disrupting the structural integrity of the implant 1110 as described herein.

In some embodiments, the flush solution 1900 can be a contrast flush. The contrast flush can be employed to verify patency. For example, a portion of the flush solution 1900 introduced upstream of the implant location within the vas deferens will be detectable within the bladder when the occlusion resulting from the implant 1110 has been removed.

In some embodiments, the first body lumen 1120 is the vas deferens and the flush solution 1900 is supplied to convey the remnant 1116 of the implant 1110 in a downstream direction within the first body lumen 1120 to a urinary tract. In some embodiments, the flush solution 1900 is conveyed to the body lumen via the entry point 1122. In some embodiments, the flush solution 1900 is supplied to the first body lumen 1120 directly via the delivery member 1500. In some embodiments, a supply tube (not shown) may be inserted into the first body lumen 1120 via the delivery member 1500 and the flush solution 1900 is conveyed into the first body lumen 1120 through the supply tube. In some embodiments, the flush solution 1900 is a saline solution, a brine solution, and/or water for injection. In some embodiments, the flush solution is a saline solution including a dye. In some embodiments, the dye is a colored dye (e.g., blue, green, orange, red, or yellow) and/or a radiological dye (e.g., iodine-based material, barium-sulfate, gadolinium, and/or saline with air mixture). In some embodiments, the flush solution 1900 includes an ultrasound-contrast agent such as microbubbles (e.g., bubbles with a diameter of about 3 micron to about 5 micron) and/or nanobubbles (e.g., bubbles with a diameter of less than or equal to about 1 micron). In some embodiments, the flush solution is a phosphate buffered saline. The phosphate buffered saline can include about 0.1 weight % to about 28 weight % sodium chloride or potassium chloride. The phosphate buffered saline can include about 0.01 molar to about 0.3 molar phosphate buffers. In some embodiments, the phosphate buffers can be one or more of Ringer's lactate, citric acid or citrate, tris-hydroxymethyl aminomethane, borate, 2-(N-morpholino) ethanesulfonic acid (MES), acetic acid or acetate.

By supplying the flush solution 1900 in a downstream direction (e.g., arrow AA), the portions of the implant 1110 are removed from the first body lumen 1120 aided by the normal flow of bodily fluids within the first body lumen 1120. For example, where the first body lumen 1120 is the vas deferens, the remnant 1116 can be flushed downstream and out of the body through the penile urethra. Because the remnant 1116 is expelled in this manner, there is no need for a filter, basket or other retrieval tool to be used to capture the flushed remnant 1116 at a downstream location.

In some embodiments, the methods described herein do not employ aspiration to withdraw the portions of the implant 1110 in the upstream direction. However, in some embodiments, an aspirating device can be introduced to the first body lumen. A suction force can be developed by the aspirating device within the first body lumen. Accordingly, the aspirating device can be used to extract at least a portion of the implant 1110, such as the remnant 1116.

In some embodiments, a method of removing an implant can include disrupting at least a portion of the implant with a pressurized fluid. FIGS. 10-15 depict a delivery member 2500 and methods that can be employed to remove implant 1110 from a body lumen (e.g., a vas deferens) without damaging the body lumen according to some embodiments. Removal (e.g., disruption) of the implant 1110 as described herein results in at least one of A) a total sperm motility of sperm passing through the vas deferens after removal of the implant being substantially similar a total sperm motility before placing of the implant in the vas deferens, B) a total sperm concentration passing through the vas deferens after the disruption of the implant being substantially similar to a total sperm concentration before placing of the implant in the vas deferens, C) an ejaculate volume passing through the vas deferens after the disruption of the implant to be substantially similar to the ejaculate volume before placing of the implant in the vas deferens, or D) a forward progression of sperm through the vas deferens after the disruption of the implant being substantially similar to a forward progression of sperm before placing of the implant in the vas deferens.

Figure 10:
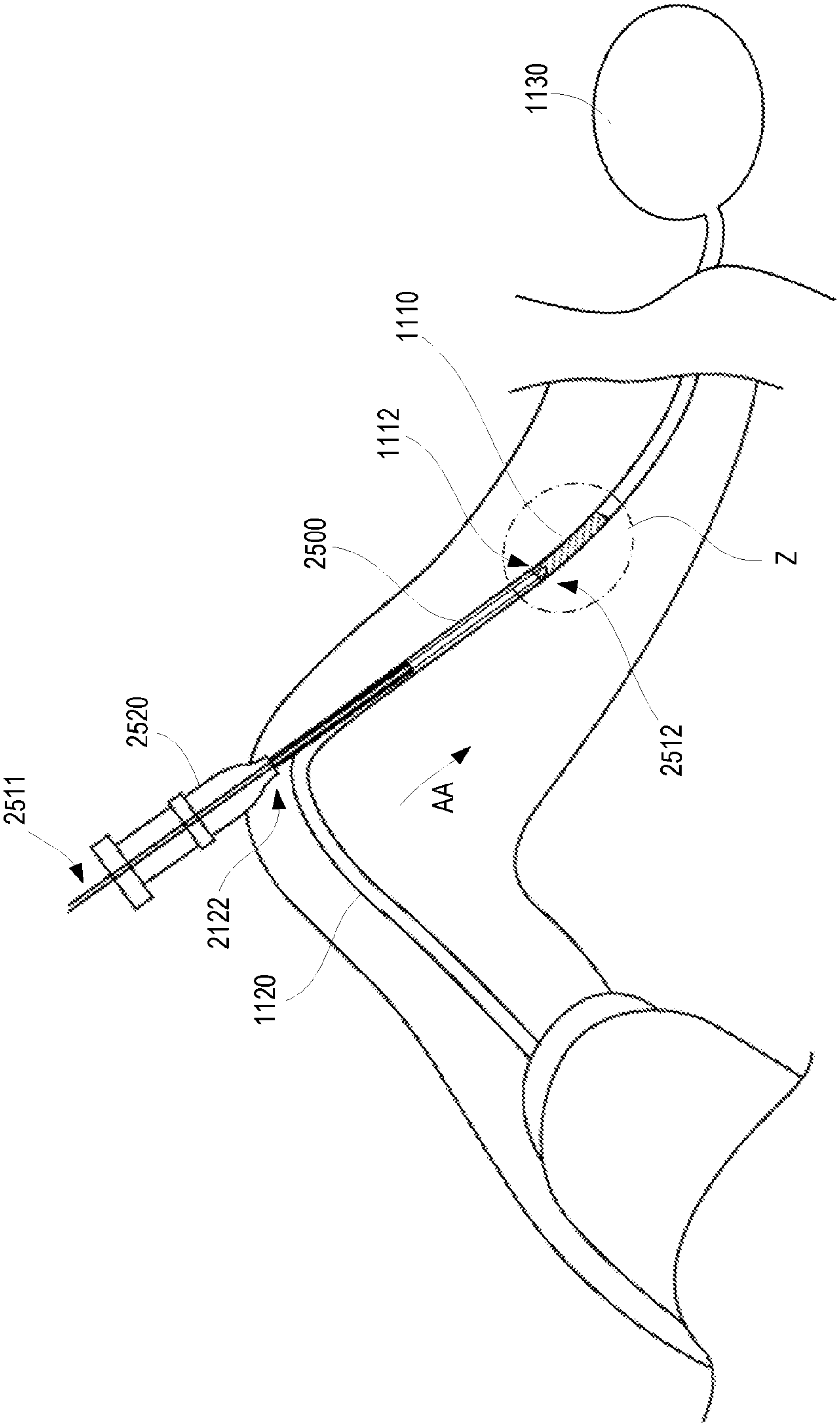
FIG. 10 is a schematic illustration of a delivery member inserted into a first body lumen occluded by an implant according to an embodiment.

FIG. 10 shows a schematic illustration of the delivery member 2500 being inserted into a first body lumen 1120 including an implant 1110 that occludes the first body lumen 1120. The insertion of the delivery member 2500 establishes an entry point 2122 into the first body lumen 1120. The delivery member 2500 can, for example, be a microcatheter or a hypo tube (e.g., hypodermic tubing, hypodermic needle tubing, or medical grade needle tubing). The delivery member can, in some embodiments, be inserted through a cannula 2520. The delivery member 2500 includes a proximal end portion 2511 and a distal end portion 2512. The proximal end portion 2511 can be coupled to a source of pressurized fluid (e.g., a pump, a syringe, a deformable volume, and/or other suitable mechanisms configured to pressurize a volume of liquid). The distal end portion 2512 of the delivery member 2500 is inserted into a first body lumen 1120 upstream of the implant 1110 and extending in a downstream direction of the first body lumen 1120, as shown by the arrow AA. As such, the delivery member 2500 is both upstream of and in fluid communication with the implant 1110. In other words, the implant 1110 is positioned downstream of the distal end portion 2512 of the delivery member 2500.

Figure 15:
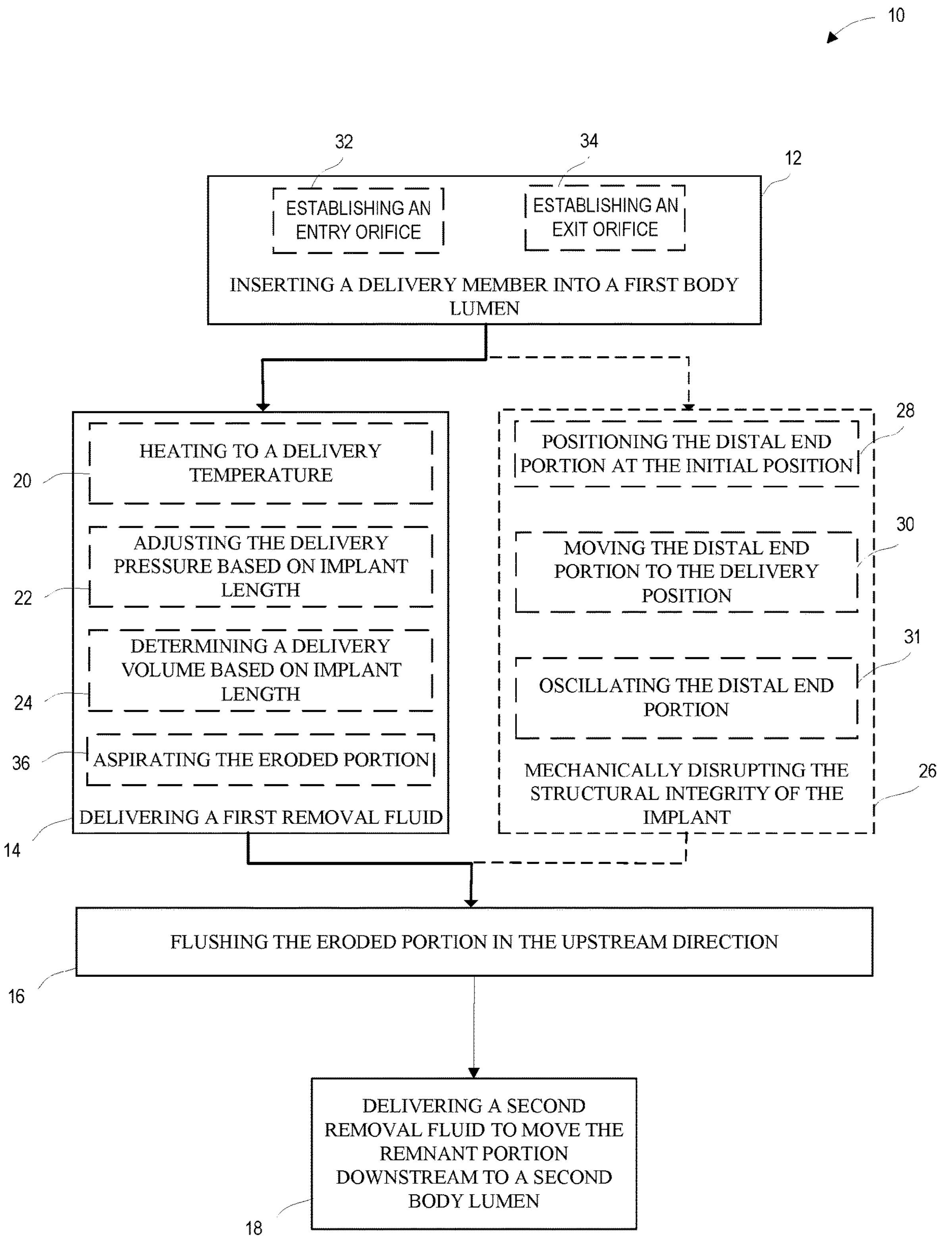
FIG. 15 is a flow chart of a method of removing a biomaterial implant from a first body lumen according to an embodiment.

In some embodiments, the delivery member 2500 can facilitate implementation of the method 10 to remove the implant 1110 from the first body lumen 1120 (e.g., from the vas deferens). FIG. 15 is a flow chart of the method 10 for removing the implant 1110 from a body lumen. In some embodiments, the body lumen can have an internal diameter that is less than 1 mm (e.g., 0.8 mm). At step 12, the delivery member 2500 is inserted into the first body lumen 1120 and placed in fluid communication with the implant 1110 (e.g., an upstream portion 1112 of the implant 1110). For example, in some embodiments, a vas deferens (e.g., the first body lumen 1120) that is occluded by the implant 1110 is cannulated upstream to the implantation site.

At step 14, a first removal fluid $RF_1$ (see FIG. 12) is delivered to the implant 1110 via the delivery member 2500. The first removal fluid $RF_1$ is delivered at a delivery pressure to cause an eroded (or fragmented) portion 1117 (FIG. 13) of the implant 1110 to be separated from a remnant portion 1116 (FIG. 13) of the implant 1110. The eroded portion 1117 can, for example, be the separated portions (e.g., fragments, chips, or flakes) of the implant 1110 that are separated from the implant 1110 by the force of the first removal fluid $RF_1$. As depicted in FIG. 13, at step 16, the eroded portion 1117 of the implant 1110 is flushed in the upstream direction of the first body lumen 1120. In other words, in so far as the first body lumen 1120 is occluded by the remnant portion 1116, the first removal fluid $RF_1$ is precluded from continuing to flow in the downstream direction. As such, the first removal fluid $RF_1$ reverses direction after affecting the implant 1110 and flows in the upstream direction (e.g., opposite of the arrow AA) of the first body lumen 1120 toward the entry point 2122. The flow of the first removal fluid $RF_1$ in the upstream direction can carry the eroded portion 1117 toward the entry point 2122 and out of the first body lumen 1120. In some embodiments, flow of the eroded portion 1117 can be additionally facilitated by aspirating the first body lumen 1120 via a vacuum source (not shown) applied at the cannula 2520.

Figure 14:
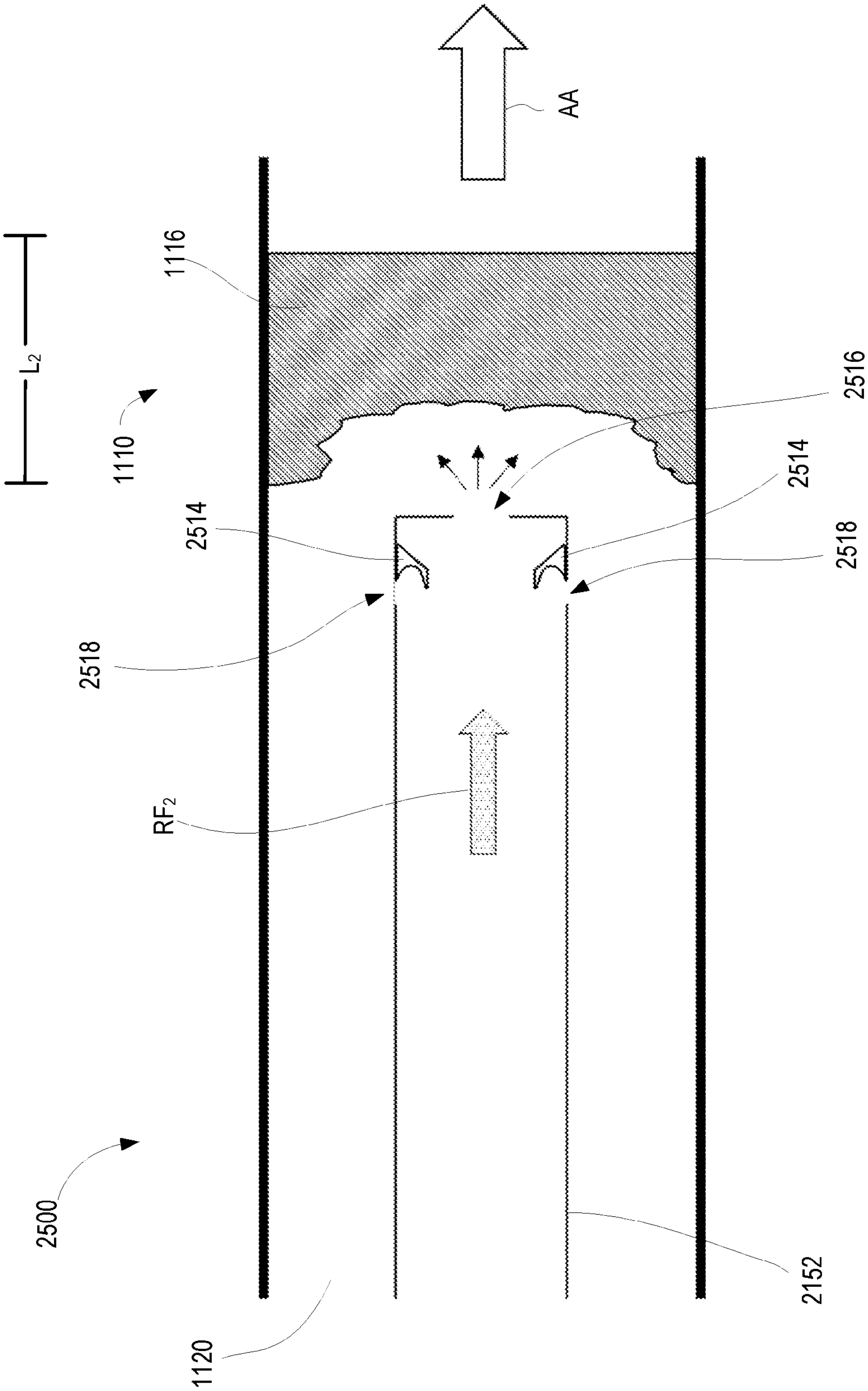
FIG. 14 is a schematic illustration of a portion of the first body lumen labeled as Region Z in FIG. 10 depicting the delivery of a removal fluid to move a remnant portion of the implant downstream.

As depicted in FIG. 14, a second removal fluid $RF_2$ is delivered, at step 18, to the first body lumen 1120 after the flushing of the eroded portion 1117 of the implant 1110 and the upstream direction. The delivery of the second removal fluid $RF_2$ moves the remnant portion 1116 of the implant 1110 downstream (e.g., in the direction indicated by arrow AA) towards a second body lumen 1130 (FIG. 10). The downstream movement of the implant 1110 is facilitated by an absence of a basket, filter, or other capture structure positioned downstream of the implant 1110 (e.g., between the remnant portion 1116 of the implant 1110 and the second body lumen 1130). The downstream direction can, for example, be the direction from the testes towards the penile urethra. The second body lumen 1130 can, for example, be a bladder or other portion of the urinary tract. From the bladder, the remnant portion 1116 can exit the body via the urethra.

In some embodiments, the implant 1110 includes an inert, non-biologic material. In some embodiments, the implant and be a hydrogel cross-linked in-situ within the vas deferens. The implant can be a cross-linked hydrogel formed from a first component and a second component. The first component can include at least one of a polyvinyl alcohol, alginate or modified alginate, chitosan or modified chitosan, polyethyleneimine, carboxymethyl cellulose, or polyethylene glycol terminated with a functional group such as a bioorthogonal functional group. The second component can include at least one of a water or buffer, water or buffer with divalent cations such as calcium, a solution of reduced hyaluronic acid, a solution of polystyrene sulfonate, a solution of gelatin, and/or polyethylene glycol terminated with a functional group, such as a bioorthogonal functional group. In some embodiments, the first component and include a multi-arm polyethylene glycol terminated with thiol, and the second component can include a multi-arm polyethylene glycol terminated with a maleimide. In some embodiments, the multi-arm polyethylene glycol terminated with thiol and/or the multi-arm polyethylene glycol terminated with a maleimide have a weight percent ranging from about 1 to about 30% in solvent. In some embodiments, the multi-arm polyethylene glycol may be linear, Y-shaped, 3-arm, 4-arm, 6-arm, or 8-arm, or hyperbranched. In some embodiments, the first component and the second component are formulated to have a pH less than about 5.25. Accordingly, exposing the implant 1110 to a solvent of sufficient concentration for a specified time interval can disrupt the cohesion and/or the adhesion of the implant 1110. Similarly, exposing the implant 1110 to a solvent of sufficient concentration can increase the porosity or mesh size of the implant. Similarly, introducing a brine solution (e.g., a solution including at least 2.5% dissolved NaCl) to the first body lumen 1120 can disrupt the structural integrity of the implant 1110.

In some embodiments the first removal fluid $RF_1$ and the second removal fluid $RF_2$ can be the same type of fluid. For example, the first removal fluid $RF_1$ can be a first volume of a saline solution and the second removal fluid $RF_2$ can be a second volume of the same saline solution delivered following the delivery of the first volume. However, in some embodiments, the first removal fluid $RF_1$ and the second removal fluid $RF_2$ can be separate fluid types. For example, the first removal fluid $RF_1$ can be a solution having a first concentration of sodium chloride and/or a first viscosity, while the second removal fluid $RF_2$ can be a solution having a second concentration of sodium chloride and/or has a second viscosity that is different than the first discussed. In some embodiments, the first removal fluid $RF_1$ and/or the second removal fluid $RF_2$ can be a solution having a viscosity that is less than the viscosity of saline at a given temperature. In some embodiments, the first removal fluid $RF_1$ and/or the second removal fluid $RF_2$ can include sodium bicarbonate, dimethyl sulfoxide, aqueous solution(s) (neutral, basic, or acidic), solution(s) containing oxidative or antioxidative compounds, solution(s) containing dissolved gases, lubricious solution(s), surfactant(s), inorganic compound(s), organic solvent(s), aqueous-organic mixture(s), emulsifier(s), lipid(s), phospholipids(s), enzyme(s), protein(s), peptide(s), polynucleotide(s), saccharides(s), polysaccharide(s), small organic molecule(s), large organic molecule(s), nanoparticle(s), microparticle(s), quantum dot(s), carbon-based material(s), and/or any combination thereof.

In some embodiments, the second removal fluid $RF_2$ can be a contrast flush. The contrast flush can be employed to verify patency. For example, a portion of the second removal fluid $RF_2$ introduced upstream of the implant location within the vas deferens will be detectable within the bladder when the occlusion resulting from the implant 1110 has been removed. The second removal fluid $RF_2$ can be a saline solution, a brine solution, and/or water for injection. In some embodiments, the flush solution is a saline solution including a dye. In some embodiments, the dye is a colored dye (e.g., blue, green, orange, red, or yellow) and/or a radiological dye (e.g., iodine-based material, barium-sulfate, gadolinium, and/or saline with air mixture). In some embodiments, the second removal fluid $RF_2$ includes an ultrasound-contrast agent such as microbubbles (e.g., bubbles with a diameter of about 3 micron to about 5 micron) and/or nanobubbles (e.g., bubbles with a diameter of less than or equal to about 1 micron). In some embodiments, the flush solution is a phosphate buffered saline. The phosphate buffered saline can include about 0.1 weight % to about 28 weight % sodium chloride or potassium chloride. The phosphate buffered saline can include about 0.01 molar to about 0.3 molar phosphate buffers. In some embodiments, the phosphate buffers can be one or more of Ringer's lactate, citric acid or citrate, tris-hydroxymethyl aminomethane, borate, 2-(N-morpholino) ethanesulfonic acid (MES), acetic acid or acetate.

In some embodiments, the first removal fluid $RF_1$ and/or the second removal fluid $RF_2$ can be heated prior to delivery. Heating the first removal fluid $RF_1$ and/or the second removal fluid $RF_2$ can lower the viscosity of the first removal fluid $RF_1$ and/or the second removal fluid $RF_2$ thereby facilitating delivery via the delivery member 2500. Additionally, heating the first removal fluid $RF_1$ and/or the second removal fluid $RF_2$ can increase the effectiveness of the respective removal fluid in affecting the implant 1110. For example, at step 20, the first removal fluid $RF_1$ is optionally heated to a delivery temperature prior to delivery. The delivery temperature can be greater than 37 degrees Celsius (e.g., at least 45 degrees Celsius). In some embodiments, the delivery temperature can be less than 65 degrees Celsius (e.g., less than or equal to 50 degrees Celsius). For example, in some embodiments the delivery temperature can be greater than or equal to 45 degrees and less than or equal to 50 degrees Celsius (e.g., in the range of 47 degrees to 48 degrees Celsius). A delivery temperature in the range of 45 degrees to 50 degrees can increase the ability of the first removal fluid $RF_1$ to separate the eroded portion 1117 of the implant 1110 relative to lower delivery temperatures and can preclude thermal damage to the surrounding tissue that could be encountered at higher delivery temperatures.

In some embodiments, the delivery pressure of the first removal fluid $RF_1$ and/or the second removal fluid $RF_2$ upon exit from the delivery member 2500 is within a specified pressure range. For example, the delivery pressure can be within a range of 2 psi to 400 psi. In some embodiments, the delivery pressure is less than a burst pressure of the first body lumen 1120.

In some embodiments, the delivery pressure is determined based, at least in part, on the length of the implant 1110 within the first body lumen 1120. In other words, the delivery pressure is determined based on a pressure-to-length ratio. For example, the delivery pressure of the first removal fluid $RF_1$ can have a pressure-to-length ratio in the range of 1 psi/cm to 4 psi/cm (e.g., in the range of 2 psi/cm to 3 psi/cm). In some embodiments, the delivery pressure of the second removal fluid $RF_2$ can have a pressure-to-length ratio in the range of 5 psi/cm to 50 psi/cm (e.g., in the range of 10 psi/cm to 40 psi/cm). For example, prior to the delivery of the first removal fluid $RF_1$, the implant can have an overall length of about 20 centimeters to 30 centimeters. Of this overall length, the proximal-most about 15 to 20 centimeters of the implant can be eroded via the first removal fluid $RF_1$. In other words, the first removal fluid $RF_1$ can be delivered (e.g., at an upstream face of the implant) at a delivery pressure in the range of about 40 psi to about 50 psi. Following the removal of the portion of the implant via the first removal fluid $RF_1$, the length of the remnant portion can be about 5 to 10 centimeters. As such, the second removal fluid $RF_2$ can be delivered at a delivery pressure in the range of about 100 psi to about 200 psi to dislodge the remnant portion and move the remnant portion downstream toward the second body lumen. Accordingly, at step 22, the method 10 includes optionally adjusting the delivery pressure based at least in part on the length of the implant 1110 within the first body limit. In other words, the delivery pressure is determined based on the prescribed pressure-to-length ratio.

In some embodiments, the first removal fluid $RF_1$ and/or the second removal fluid $RF_2$ can be delivered at a delivery pressure that oscillates between pressures within a range. Said another way, in some embodiments the delivery pressure of the first removal fluid $RF_1$ and/or the second removal fluid $RF_2$ can be pulsed to enhance the effectiveness of the methods described herein. The pulsation frequency of the pressure can be within any suitable range, such for example between 1 Hz and 100 Hz.

In some embodiments, delivering the first removal fluid $RF_1$ and/or the second removal fluid $RF_2$ includes delivering a delivery volume of the respective fluid. The delivery volume can be determined based, at least in part, on the length of the implant 1110 within the first body lumen 1120. In other words, the delivery volume can be determined based on a volume-to-length ratio. For example, the delivery volume can have a volume-length ratio in the range of 1.0 mL/cm and 30 mL/cm. As such, at step 24, the method 10 includes optionally determining a delivery volume of the first removal fluid $RF_1$ based, at least in part, on the length of the implant 1110 within the first body lumen 1120. The length of the implant can, for example, be determined based on the volume of the hydrogel introduced at time of implantation and a measurement of the inner diameter of the first body lumen 1120. The length of the implant can also be estimated based on the volume of the hydrogel introduced at time of implantation and an average inner diameter of a representative first body lumen (e.g., the average inner diameter of a vas deferens according to historical anatomical data).

Figure 11:
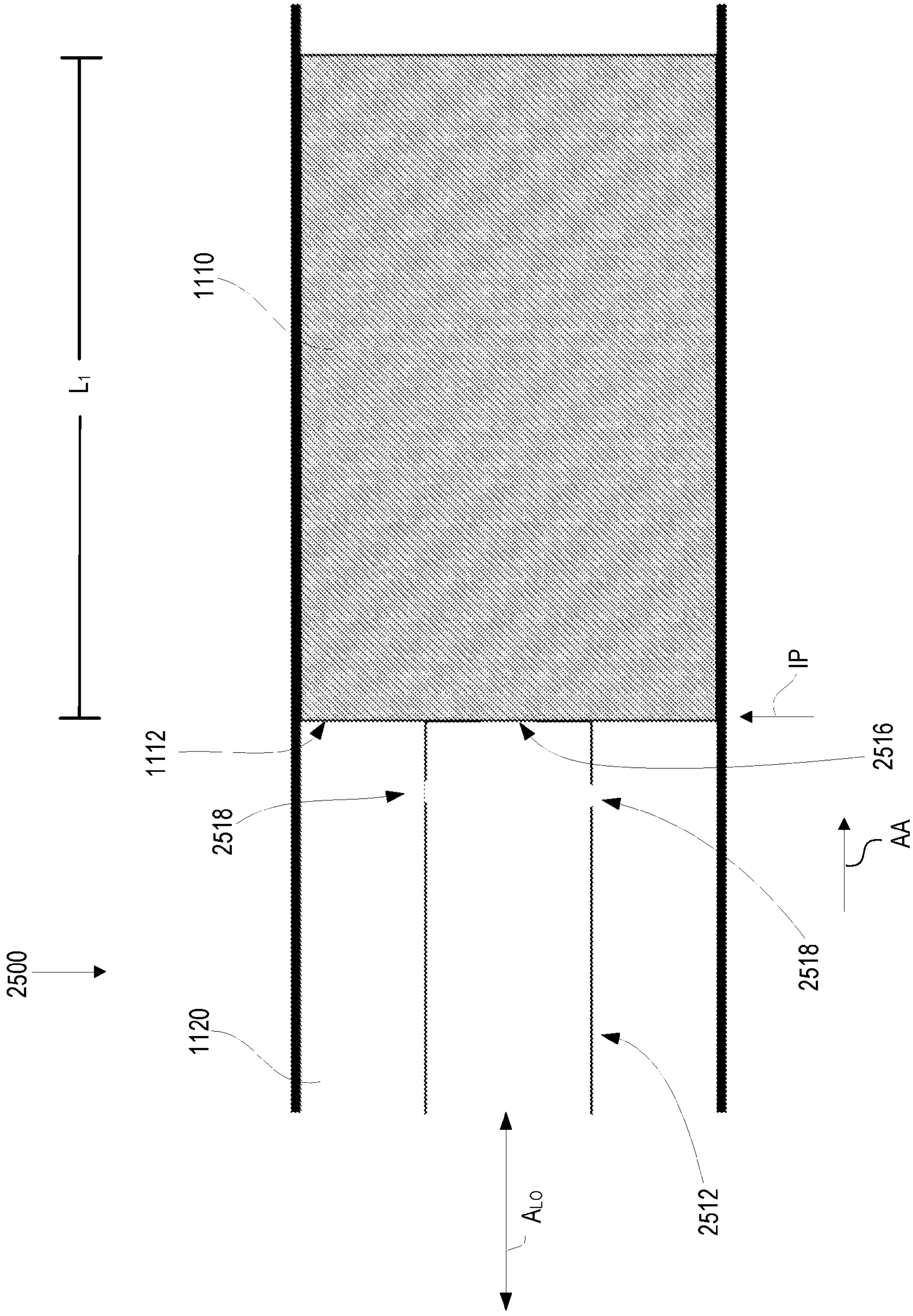
FIG. 11 is a schematic illustration of a portion of the first body lumen labeled as Region Z in FIG. 10 depicting a distal end portion of the delivery member at an initial position in contact with the implant.
Figure 12:
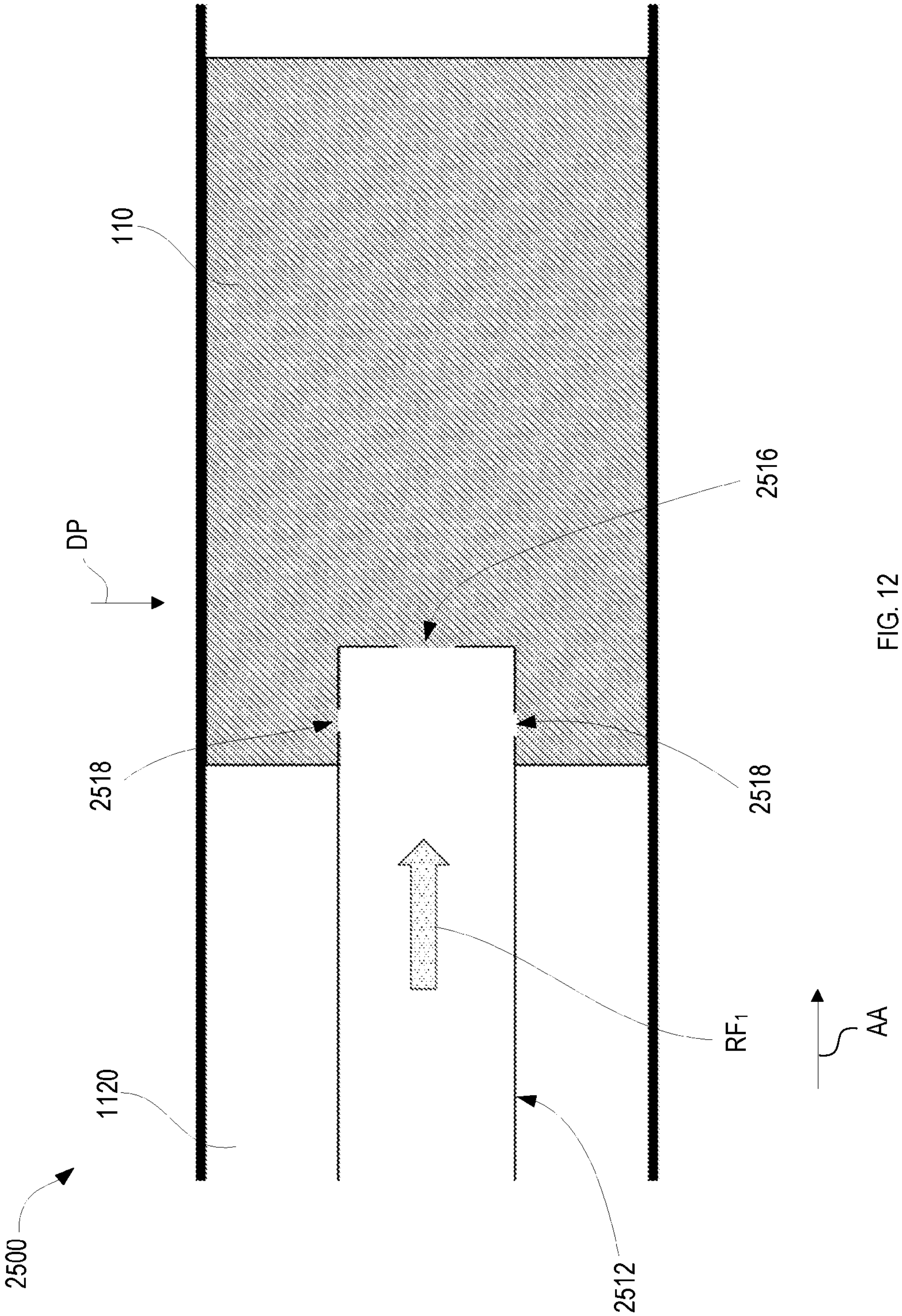
FIG. 12 is a schematic illustration of a portion of the first body lumen labeled as Region Z in FIG. 10 depicting the distal end portion of the delivery member at a delivery position.
Figure 13:
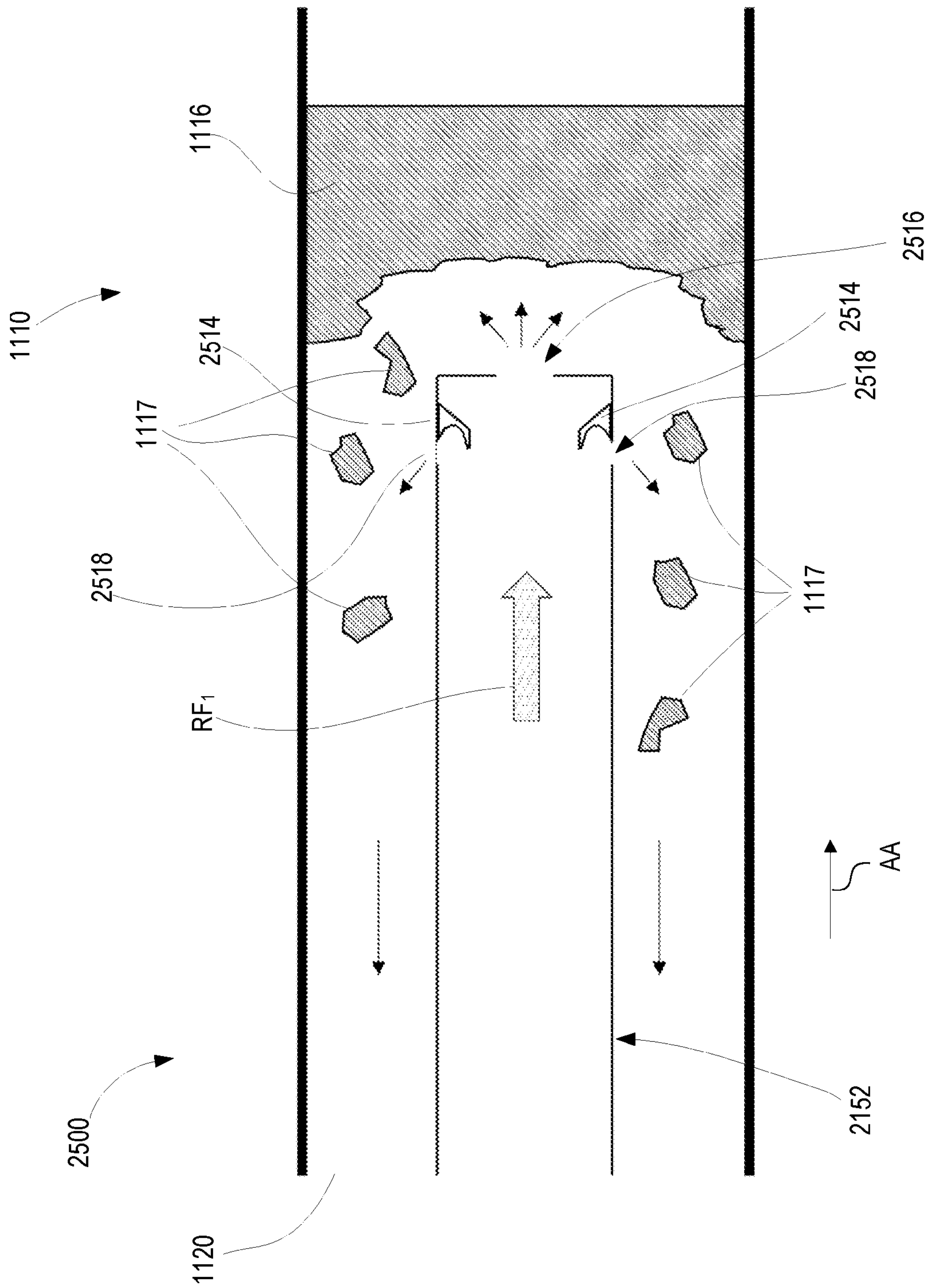
FIG. 13 is a schematic illustration of a portion of the first body lumen labeled as Region Z in FIG. 10 depicting the separation of an eroded portion of the implant.

As depicted in FIGS. 11 and 12, in some embodiments, the method 10 includes optionally mechanically disrupting, at step 26, the structural integrity of the implant 1110 during delivery of the first removal fluid $RF_1$. Mechanically disrupting the implant 1110 can correspond to the disruption of the cohesion of the implant 1110 by the delivery member during the delivery of the first removal fluid $RF_1$. Mechanically disrupting the cohesion of the implant 1110 can increase the ability of the first removal fluid $RF_1$ to separate the eroded portion 1117 from the remnant portion 1116. For example, the mechanical disruption of the implant 1110 can cause the implant 1110 to develop a series of micro cracks through which the first removal fluid $RF_1$ can propagate and hydraulically separate a plurality of portions of the implant 1110.

In some embodiments, mechanically disrupting the structural integrity of the implant 1110 can include mechanically disrupting the structural integrity of the implant 1110 with the delivery member 2500 during the delivery of the first removal fluid $RF_1$. As depicted in FIG. 11, in some embodiments, the distal end portion 2512 of the delivery member 2500 is positioned, at step 28, at an initial position IP in contact with the implant 1110. The initial position IP can correspond to an insertion length of the delivery member 2500 at which a resistance to further distal movement of the distal end portion 2512 of the delivery member 2500 is first encountered. As depicted in FIG. 12, the distal end portion 2512 is moved, at step 30, in the distal direction from the initial position IP into the implant 1110 to a delivery position DP. The distal movement beyond the initial position IP can have a magnitude that is in the range of about 0.5 and 10 percent of the implant length. For example, in some embodiments, the delivery position DP is displaced between 1 millimeter and 10 millimeters in the distal direction from the initial position IP. At step 31, the distal end portion 2512 is oscillated between the initial position IP and the delivery position DP to mechanically disrupt the structural integrity of the implant 1110 during delivery of the first removal fluid $RF_1$. In other words, the first removal fluid $RF_1$ is introduced at the delivery position DP, at the initial position IP, and at all positions therebetween in conjunction with the oscillation of the distal end portion 2512.

In some embodiments, the delivery member 2500 is operably coupled to a control device (not shown). The control device includes at least one sensor. The sensor(s) is configured to monitor an operating condition of the distal end portion 2512 of the delivery member. For example, in some embodiments, the sensor(s) of the control device is an accelerometer. The accelerometer can be configured to detect an oscillation of the distal end portion 2512 (e.g., an oscillation between the initial position IP and the delivery position DP). As such, the control device can limit the flow of the first removal fluid $RF_1$ in response to a signal from the accelerometer indicating that the distal end portion 2512 of the delivery member 2500 is stationary. By limiting the flow of the first removal fluid $RF_1$ on a condition that the distal end portion 2512 is stationary, the control device can limit a pressure buildup at the point of departure of the first removal fluid $RF_1$ from the distal end portion 2512 and can, therefore, maintain the delivery pressure of the first removal fluid $RF_1$ at a magnitude that is less than the first pressure of the first body lumen 1120. In some embodiments, the sensor(s) can be a load sensor, such as a spring, a load cell, or other suitable sensor, for detecting a load placed on the distal end portion 2512 of the delivery member 2500. The load sensor can be configured to detect a condition in which the distal end portion 2512 is in contact (e.g., as depicted in FIG. 11) with the implant 1110 based, at least in part, on the stiffness of the implant 1110. The implant 1110 can, for example, have a stiffness that is stiffer than a blood clot and the structure forming the first body lumen 1120. The control device can be configured to produce an indication of contact between the distal end portion 2512 and the implant 1110 based on the detection by the load sensor. As such, the control device can be configured to detect a condition in which the distal end portion 2512 is at the initial position IP.

Insofar as the eroded portion 1117 of the implant 1110 is flushed in an upstream direction, it may be desirable to establish an exit point for the eroded portion 1117 at a location that is upstream of the implant 1110. Accordingly, in some embodiments inserting the delivery member 2500 into the first body lumen 1120 includes inserting the delivery member 2500 through an incision in the first body lumen 1120. The incision can be oversized sized to facilitate the passage of the eroded portion 1117 while the delivery member 2500 is in situ. For example, in some embodiments, the incision has a length that is at least two times (e.g., five times) the outer diameter of the delivery member 2500. In some embodiments, the method 10 optionally includes establishing, at step 32, an entry orifice in the first body lumen 1120 at a location that is upstream of the implant 1110. The entry orifice can be sized to receive the delivery member 2500. The method 10 also optionally includes, at step 34, establishing an exit orifice in the first body lumen 1120 at a location that is upstream of the implant 1110 and downstream of the entry orifice. The exit orifice is sized to facilitate passage of the eroded portion 1117 of the implant 1110. In some embodiments, inserting the delivery member 2500 into the first body lumen 1120 includes inserting the delivery member through the cannula 2520 (FIG. 10) positioned at least partially in the first body lumen 1120. The cannula 2520 has an inner diameter that is sized to receive an outer diameter of the delivery member 2500 while still permitting passage of the eroded portion 1117. Said another way, the cannula 2520 is oversized such that there is sufficient space between an inner wall of the cannula and the delivery member 2500 to permit passage (e.g., exit from the first body lumen 1120) of the eroded portion 1117 while the delivery member 2500 is in situ.

As stated previously, in some embodiments, the delivery member 2500 can, for example, be a microcatheter or a hypo tube (e.g., hypodermic tubing, hypodermic needle tubing, or medical grade needle tubing). In some embodiments, delivery member has an outer diameter that is less than 1.0 millimeter (e.g., less than or equal to 0.9 millimeters) and greater than or equal to 0.5 millimeters (e.g., greater than or equal to 0.7 mm) to facilitate entry into a vas deferens (e.g., a body lumen having an inner diameter of 1.0 millimeter or less). The delivery member 2500 can include an integrated steerable or angled tip and a lubricious coating. As depicted in FIGS. 13 and 14, in some embodiments, the delivery member 2500 can include at least one flow element 2514. The flow element(s) 2514 can be positioned and/or configured to modify the flow of the first removal fluid $RF_1$ within and/or exiting from the delivery member 2500. For example, the flow element(s) 2514 can redirect a portion of the first removal fluid $RF_1$ in the upstream direction of the first body lumen 1120 to facilitate flushing the eroded portion 1117. As an additional example, the flow element(s) 2514 can shape the flow of the first removal fluid $RF_1$ by imparting a rotational vector to the flow and/or establishing a laminar flow region.

In some embodiments, the distal end portion 2512 defines a longitudinal axis $A_{LO}$ (FIG. 11). As depicted in FIGS. 11-14, the distal end portion, in some embodiments, defines a distal orifice 2516. The distal orifice 2516 is axially aligned with the longitudinal axis $A_{LO}$. As such, a portion of the first removal fluid $RF_1$ and/or the second removal fluid $RF_2$ exiting the distal orifice 2516 at the delivery pressure is directed into the implant 1110 in the downstream direction. In some embodiments, the distal end portion 2512 also defines at least one radial orifice 2518. The radial orifice(s) 2518 is positioned proximal to the distal orifice 2516. As such, in some embodiments, delivering the first removal fluid $RF_1$ includes delivering a portion of the first removal fluid $RF_1$ via the radial orifice(s) 2518 such that the portion of the first removal fluid $RF_1$ is directed radially outward from the longitudinal axis $A_{LO}$. The radial orifice(s) 2518 can thus facilitate the separation of the eroded portion 1117 and/or the flushing of the eroded portion 1117 once separated from the remnant portion 1116.

In some embodiments, the delivery member 2500 is a dual-lumen delivery member 2500. The dual-lumen delivery member can have a first member lumen and a separate second member lumen that extend along the longitudinal length of the delivery member 2500. In some embodiments, the first removal fluid $RF_1$ can be delivered via the first member lumen while a separate flush fluid is delivered via the second member lumen. In such an embodiment, the first removal fluid $RF_1$ can be delivered at a first delivery pressure and the flush fluid can be delivered at a second, lesser delivery pressure to facilitate flushing the eroded portion 1117 in the upstream direction. In some embodiments however, the second member lumen can be used to aspirate the first body lumen 1120 during delivery of the first removal fluid $RF_1$. Accordingly, at step 36, the method 10 optionally includes aspirating the eroded portion 1117 of the implant 1110 via the second lumen during the delivery of the first removal fluid $RF_1$ via the first member lumen. In some embodiments, the first member lumen and the second member lumen are arranged in a side-by-side configuration. However, in some embodiments, the second member lumen surrounds the first member lumen. In other words, the first member lumen and the second member lumen can be axially aligned in a concentric arrangement.

Figure 16:
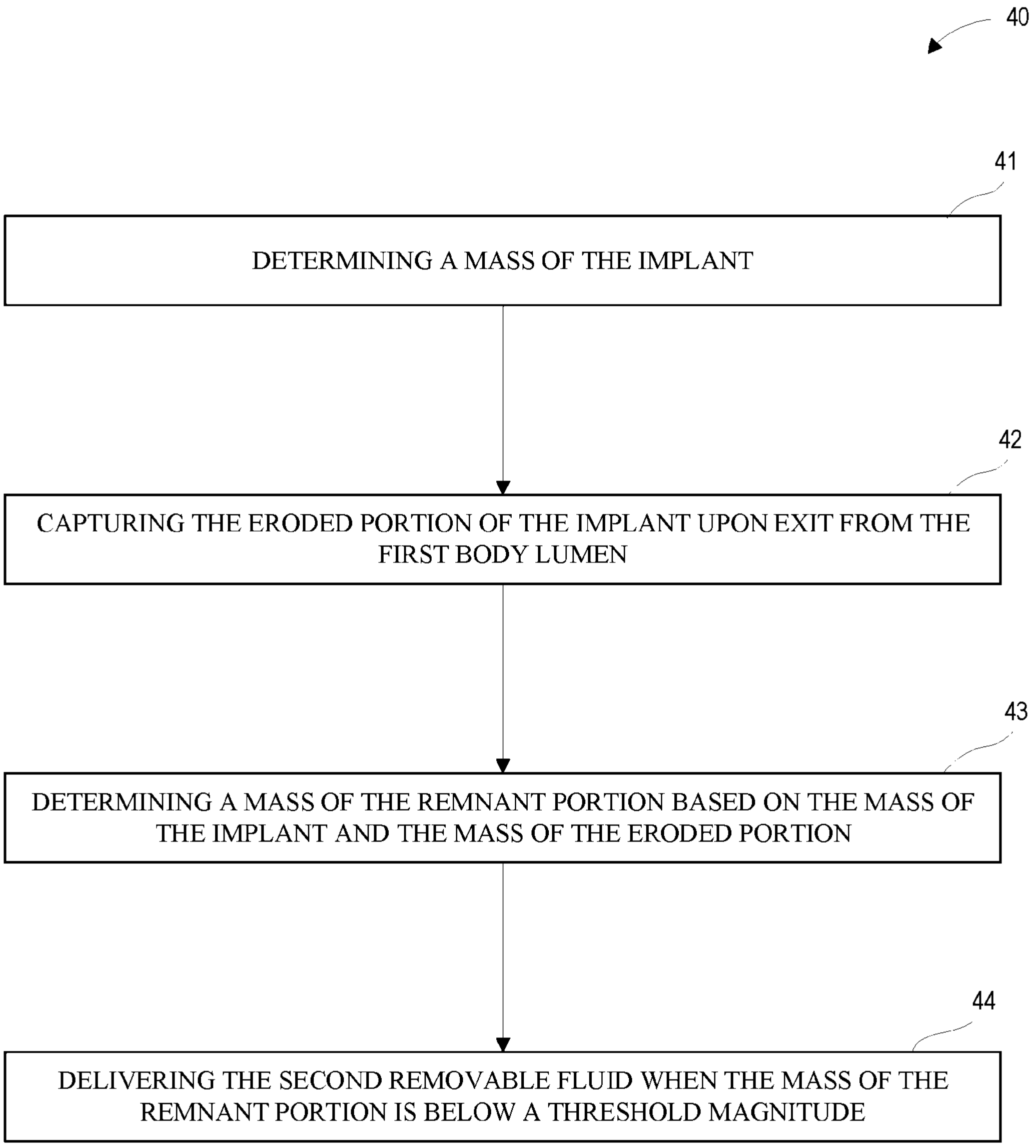
FIG. 16 is a flow chart of a method of delivery of a removal fluid.

FIG. 16 depicts a method 40 for determining when to deliver the second removal fluid $RF_2$ to move the remnant portion 1116 downstream to the second body lumen 1130 according to an embodiment. The method 40 can be executed in conjunction with the method 10 to remove the implant 1110 from the first body lumen 1120. The method 40 can be performed in connection with any of the methods for disrupting an implant described herein (e.g., producing an eroded portion via mechanical disruption, hydraulic disruption, chemical disruption or a combination of any of these). As depicted at step 41, in some embodiments, the method 40 includes determining a mass of the implant 1110. The mass of the implant 1110 can, for example, be determined based on the recorded (e.g., in a medical record) volume of the hydrogel dispensed at time of implantation to form the implant 1110. In other embodiments, the mass of the implant 1110 can be determined based on size measurements (e.g., length and diameter) from imaging results. At step 42, the method 40 includes capturing the eroded portion 1117 of the implant 1110 that is flushed upstream upon its exit from the first body lumen 1120. The capturing of the eroded portion 1117 can, for example, be accomplished via a catch basin or a filter. Once captured, the eroded portion 1117 can be weighed to determine the mass of the eroded portion. In some embodiments, a corrective factor can be applied to the weighed mass to account for uncaptured portions of the implant 1110. At step 43, the mass of the remnant portion 1116 is determined based on the mass of the implant 1110 (and at step 41) and the mass of the eroded portion 1117 captured upon exit from the first body lumen 1120. At step 44, the method 40 includes delivering the second removal fluid $RF_2$ on a condition that the mass of the remnant portion 1116 is below a threshold magnitude. In other words, the second removal fluid $RF_2$ can be delivered to move the remnant portion 1116 downstream once the mass of the remnant portion 1116 has been reduced to an amount that is predicted to be responsive to the force (e.g., to move) applied by the second removal fluid $RF_2$.

Figure 17:
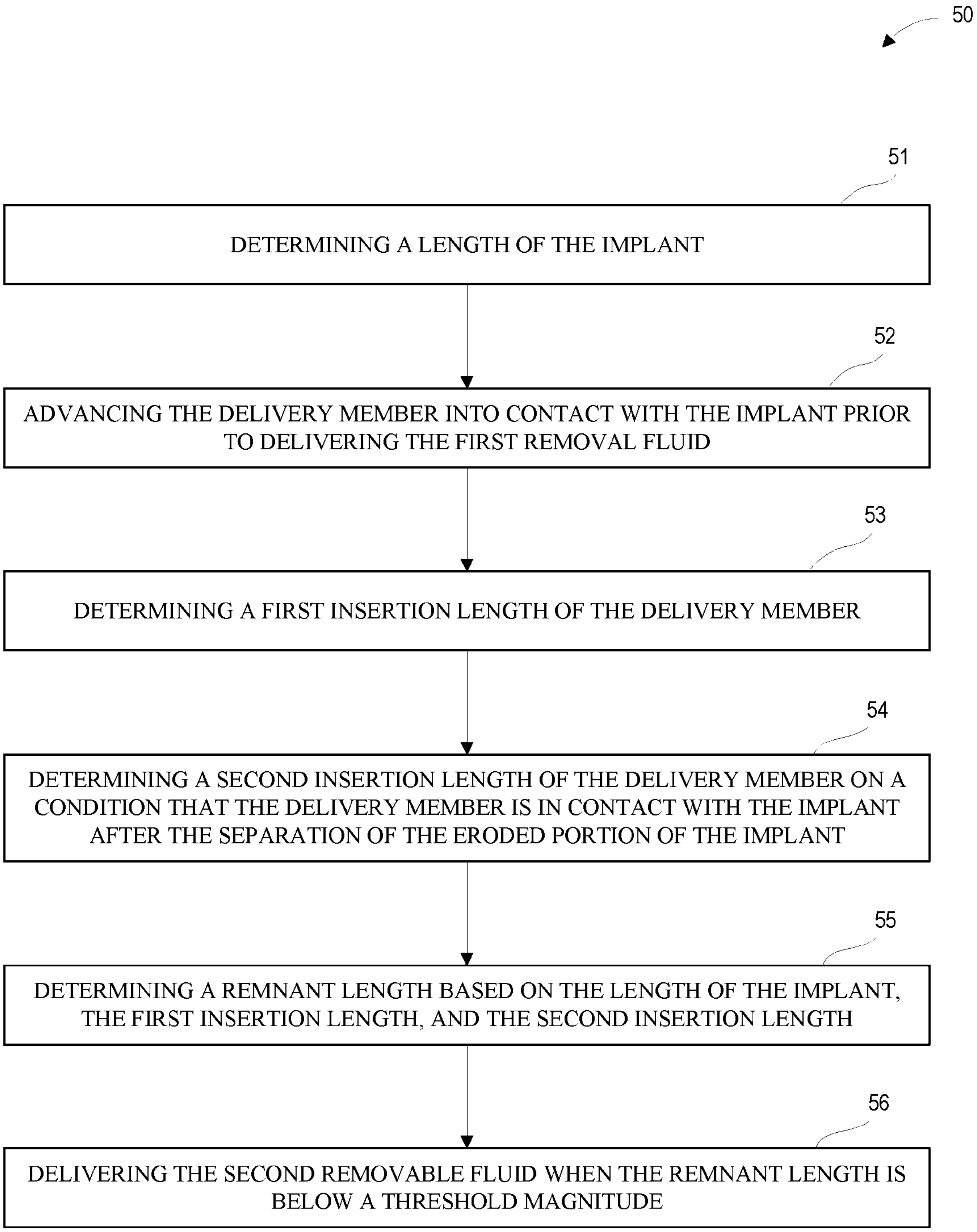
FIG. 17 is a flow chart of a method of delivery of a removal fluid.

FIG. 17 depicts a method 50 for determining when to deliver the second removal fluid $RF_2$ to move the remnant portion 1116 downstream to the second body lumen 1130 according to an embodiment. The method 50 can be performed in connection with any of the methods for disrupting an implant described herein (e.g., producing an eroded portion via mechanical disruption, hydraulic disruption, chemical disruption or a combination of any of these). The method 50 can be executed in conjunction with the method 10 to remove the implant 1110 from the first body lumen 1120. As depicted at step 51, the method 50 includes determining a length $L_1$ (FIG. 11) of the implant 1110 (e.g., the length of the implant at time of implantation and prior to the delivery of the first removal fluid $RF_1$). The mass of the implant 1110 can, for example, be determined based on the recorded (e.g., in a medical record) volume of the hydrogel dispensed at time of implantation to form the implant 1110 and the observed diameter inner diameter of the first body lumen 1120 during implantation. At step 52, the method 50 includes advancing the delivery member 2500 within the first body lumen 1120 and into contact with the implant 1110 prior to delivering the first removal fluid $RF_1$, as depicted in FIG. 11. At step 53, the method 50 includes determining a first insertion length of the delivery member 2500 on a condition that the delivery member 2500 is in contact with the first implant. At step 54, the method 50 includes determining a second insertion length of the delivery member 2500 on a condition that the delivery member is in contact with the implant 1110 after the separation of the eroded portion 1117. The first insertion length and the second insertion length can, for example, be determined based on indicia visible on the outer surface of the delivery member 2500. At step 55, the method 50 includes determining a remnant length $L_2$ (FIG. 14) based on the length $L_1$ of the implant 1110, the first insertion length, and the second insertion length. In other words, the shortening of the implant 1110 in response to the removal of the eroded portion 1117 corresponds to an increase in available travel of the distal end portion 2512 in the proximal direction within the first body lumen 1120. At step 56, the method 50 includes delivering the second removal fluid $RF_2$ when the remnant length $L_2$ is below a threshold magnitude. In other words, the second removal fluid $RF_2$ can be delivered to move the remnant portion 1116 downstream once the length of the remnant portion 1116 has been reduced to an amount that is predicted to be responsive to the force (e.g., to move) applied by the second removal fluid $RF_2$.

In some embodiments, the implant 1110 has a stored moduli that is greater than about 1000 Pa. For example, the implant can have a storage modulus between about 2,000 Pa and about 20,000 Pa. As such, the implant 1110 presents a greater resistance to disruption than would a blood clot, plaque buildup, or other obstruction encountered during a vascular operation.

In some embodiments, an apparatus for the removal of an implant from a lumen includes a delivery member sized to be received by a cannula and inserted into a first lumen. The delivery member is in fluid communication with an implant within the first lumen on a condition that the delivery member is inserted into the first lumen. A fluid reservoir is fluidically coupled to the delivery member. A removal fluid is contained by the fluid reservoir. The removal fluid is configured to be delivered to the implant via the delivery member at a delivery pressure to cause an eroded portion of the implant to be separated from a remnant portion of the implant. The removal fluid is also configured to flush the eroded portion of the implant in an upstream direction of the first lumen. Additionally, the removal fluid is configured to move the remnant portion of the implant downstream to a second lumen following the eroding of the eroded portion.

In some embodiments, a system for the removal of an implant from a lumen includes a delivery member sized to be received by a cannula and inserted into a first lumen. The delivery member is configured to be in fluid communication with an implant within the first lumen on a condition that the delivery member is inserted into the first lumen. A fluid reservoir is fluidically coupled to the delivery member. A removal fluid is contained by the fluid reservoir. The system is configured to deliver the removal fluid to the implant via the delivery member at a delivery pressure to cause an eroded portion of the implant to be separated from a remnant portion of the implant. The system is also configured to cause the removal fluid to flush the eroded portion of the implant in an upstream direction of the first lumen. Additionally, the system is configured to move the remnant portion of the implant downstream to a second lumen following the eroding of the eroded portion.

In some embodiments, the invention also pertains to the use of an implant removal system, the implant removal system comprising a delivery member sized to be received by a cannula and inserted into a first lumen. The delivery member is configured to be in fluid communication with an implant within the first lumen on a condition that the delivery member is inserted into the first lumen. A fluid reservoir is fluidically coupled to the delivery member. A removal fluid is contained by the fluid reservoir.

A number of embodiments have been described. Nevertheless, it will be understood that various modifications may be made without departing from the spirit and scope of the invention. In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other embodiments are within the scope of the following claims.

While various embodiments of the invention have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above. Any of the components and sub-components described herein can be included in any of the embodiments unless mutually exclusive. For example, in some embodiments, the methods may be performed successively on multiple body lumens, such as a first vas deferens and a second vas deferens of a patient.

In some embodiments, biomaterial forming the implant in the body lumen is formed from one or more precursors. For example, two macromer solutions are injected that crosslink with each other to form a hydrogel material. The delivery apparatus injects solutions into the body, such that the solutions form a hydrogel in situ. In some embodiments, the delivery apparatus is used to inject the formed biomaterial into the body, e.g. cross-linked hydrogel. The hydrogel may continue to gel and/or cross-link in situ once injected or can be completely gelled or cross-linked by the time it exits the delivery apparatus. In this regard, the delivery apparatus facilitates the merging or mixing of the two or more different solutions into a single stream.

In some embodiments, the biomaterial forming the implant in the body lumen includes one or more of natural or synthetic monomers, polymers or copolymers, biocompatible monomers, polymers or copolymers, such as polystyrene, neoprene, polyetherether ketone (PEEK), carbon reinforced PEEK, polyphenylene, polyetherketoneketone (PEKK), polyaryletherketone (PAEK), polyphenylsulphone, polysulphone, polyurethane, polyethylene, low-density polyethylene (LDPE), linear low-density polyethylene (LLDPE), high-density polyethylene (HDPE), polypropylene, polyetherketoneetherketoneketone (PEKEKK), nylon, fluoropolymers such as polytetrafluoroethylene (PTFE or TEFLON®), TEFLON® TFE (tetrafluoroethylene), polyethylene terephthalate (PET or PETE), TEFLON® FEP (fluorinated ethylene propylene), TEFLON® PFA (perfluoroalkoxy alkane), and/or polymethylpentene (PMP) styrene maleic anhydride, styrene maleic acid (SMA), polyurethane, silicone, polymethyl methacrylate, polyacrylonitrile, poly (carbonate-urethane), poly(vinylacetate), nitrocellulose, cellulose acetate, urethane, urethane/carbonate, polylactic acid, polyacrylamide (PAAM), poly(N-isopropylacrylamine) (PNIPAM), poly(vinylmethylether), poly(ethylene oxide), poly(ethyl (hydroxyethyl) cellulose), poly(2-ethyl oxazoline), polylactide (PLA), poly glycolide (PGA), poly(lactide-co-glycolide) PLGA, poly(e-caprolactone), polydiaoxanone, polyanhydride, trimethylene carbonate, poly(β-hydroxybutyrate), poly(g-ethyl glutamate), poly(DTH-iminocarbonate), poly(bisphenol A-iminocarbonate), poly (orthoester) (POE), polycyanoacrylate (PCA), polyphosphazene, polyethyleneoxide (PEO), polyethylene glycol (PEG) or any of its derivatives, polyacrylacid (PAA), polyacrylonitrile (PAN), polyvinylacrylate (PVA), polyvinylpyrrolidone (PVP), polyglycolic lactic acid (PGLA), poly(2-hydroxypropyl methacrylamide) (pHPMAm), poly (vinyl alcohol) (PVOH), PEG diacrylate (PEGDA), poly (hydroxyethyl methacrylate) (pHEMA), N-isopropylacrylamide (NIPA), polyoxazoline (POx), poly(vinyl alcohol) poly(acrylic acid) (PVOH-PAA), collagen, silk, fibrin, gelatin, hyaluronic acid, cellulose, chitin, dextran, casein, albumin, ovalbumin, heparin sulfate, starch, agar, heparin, alginate, fibronectin, keratin, pectin, elastin, ethylene vinyl acetate, ethylene vinyl alcohol (EVOH), polyethylene oxide, PLLA or PLA (poly(L-lactide) or poly(L-lactic acid)), poly (D,L-lactic acid), poly(D,L-lactide), poly dimethylsiloxane or dimethicone (PDMS), poly(isopropyl acrylate) (PIPA), polyethylene vinyl acetate (PEVA), PEG styrene, polytetrafluoroethylene RFE such as TEFLON® RFE or KRYTOX® RFE, fluorinated polyethylene (FLPE or NALGENE®), methyl palmitate, temperature responsive polymers such as poly(N-isopropylacrylamide) (NIPA), polycarbonate, polyethersulfone, polycaprolactone, polymethyl methacrylate, polyisobutylene, nitrocellulose, medical grade silicone, cellulose acetate, cellulose acetate butyrate, polyacrylonitrile, poly(lactide-co-caprolactone (PLCL), and/or chitosan.

In some embodiments, the dissolving solution for the polymer component(s) may be aqueous buffers (pH range 1-14): phosphate, citrate, acetate, histidine, lactate, tromethamine, gluconate, aspartate, glutamate, tartrate, succinate, malic acid, fumaric acid, alpha-ketoglutaric, and/or carbonate. Non-aqueous solvents include: dimethyl isosorbide, glycofurol 75, PEG 200, diglyme, tetrahydrofurfuryl alcohol, ethanol, acetone, solketal, glycerol formal, dimethyl sulfoxide, propylene glycol, ethyl lactate, N-methyl-2-pyrrolidone, dimethylacetamide, methanol, isopropanol, 1,4-butanediol, ethyl acetate, toluene, acetonitrile. In some embodiments, when the polymer component is dissolved, the viscosity of the solution(s) that make up the biomaterial may range from about 0.1 to about 250,000 cP, such as about 0.5 to about 200,000 cP, about 1 to about 150,000 cP, about 5 to about 100,000 cP, about 10 to about 75,000 cP, about 20 to about 50,000 cP, about 50 to about 25,000 cP, about 100 to about 10,000 cP, about 500 to about 7,500 cP, or about 1,000 to about 5,000 cP, or any viscosity in between. The density of the solution may range from about 0.1 to about 20,000 kg/$m^3$, such as about 1 to about 15,000 kg/$m^3$, about 5 to about 12,500 kg/$m^3$, about 10 to about 10,000 kg/$m^3$, about 100 to about 5,000 kg/$m^3$, about 500 to about 2,5000 kg/$m^3$, or about 1,000 to about 1,500 kg/$m^3$, or any density in between. The temperature during extrusion may range from about 2 to about 45° C., such as about 5 to about 40° C., about 10 to about 38° C., about 15 to about 37° C., about 20 to about 36° C., about 25 to about 35° C., about 30 to about 34° C., or about 31 to about 33° C., or any temperature in between. The pH of the solution(s) may range from 1-14. The ionic strength of the solution(s) may range from about 1 nM to about 70 M, such as about 5 nM to about 60 M, about 10 nM to about 50 M, about 20 nM to about 25 M, about 50 nM to about 15 M, about 75 nM to about 10 M, 100 nM to about 5 M, or about 500 nM to about 2.5 M, or any molarity in between.

In some embodiments, if two components are injected to form the biomaterial, then the ratio of the components may be varied such as 1:1, 2:1, 1:2, 3:1, 1:3, 4:1, 1:4, and up to 10:1 or 1:10. The gelation time of the biomaterial may range from about 0.001 seconds to about 60 minutes, such as about 1 second to about 45 minutes, about 5 seconds to about 30 minutes, about 10 seconds to about 15 minutes, about 20 seconds to about 10 minutes, about 30 seconds to about 8 minutes, about 45 seconds to about 5 minutes, about 1 minute to about 3 minutes, or about 1.5 minutes to about 2.5 minutes, or any range in between. The length of the formed biomaterial may range from about 0.1 to about 60 cm, such as about 0.2 to about 50 cm, about 0.3 to about 40 cm, about 0.4 to about 30 cm, about 0.5 to about 20 cm, about 0.6 to about 15 cm, about 0.8 to about 10 cm, about 0.9 to about 5 cm, about 1.2 to about 4 cm, about 1.4 to about 3 cm, about 1.6 to about 2.5 cm, or about 1.8 to about 2.2 cm, or any range in between. The volume of the formed biomaterial may range from about 0.001 to about 100 mL, such as about 0.005 to about 90 mL, about 0.01 to about 80 mL, about 0.05 to about 70 mL, about 0.1 to about 60 mL, about 0.2 mL to about 50 mL, about 0.25 to about 40 mL, about 0.4 to about 30 mL, about 0.5 to about 20 mL, about 0.7 to about 10 mL, about 0.9 to about 5 mL, about 1.1 to about 4 mL, about 1.4 to about 3 mL, or about 2 mL to about 2.5 mL, or any range in between.

In some embodiments, the biomaterial forming the implant swells within the implantation space to lock or secure its placement. For example, a biomaterial in the form of a hydrogel may swell from about 1.5× to about 10× its initial volume, such as about 2× to about 8×, about 2.5× to about 7×, about 3× to about 6×, or about 4× to about 5×. In some embodiments, the extruded biomaterial conforms to the space it is injected into. In some embodiments, the swelling of the biomaterial does not change volume within the implantation space, or shrinks to conform to a volume of the implantation space. In some embodiments, the implant is injected or delivered as a pre-formed biomaterial (does not cross-link, form, or gel in situ). Once injected, the biomaterial may or may not react with the implantation space. If a reaction does occur, it may be covalent or non-covalent. In some embodiments, the biomaterial adhesively interacts within the implantation space.

Although various embodiments have been described as having particular features and/or combinations of components, other embodiments are possible having a combination of any features and/or components from any of embodiments where appropriate.

What is claimed is:

1. A method of removing an implant from a body lumen, comprising:
- inserting a delivery member into the body lumen, the delivery member being in fluid communication with the implant, the body lumen having a maximal inner diameter in a range of 0.75 mm to 2.0 mm;
- advancing a guidewire through the delivery member and through the implant;
- advancing a microcatheter over the guidewire through the implant;
- positioning a distal end portion of the microcatheter beyond the implant;
- advancing a retrieval tool through the microcatheter to a position that is beyond the distal end portion of the microcatheter;
- transitioning the retrieval tool to an expanded configuration;
- engaging a portion of the implant with the retrieval tool in the expanded configuration;
- extracting at least a first portion of the implant from the body lumen by moving the retrieval tool;
- exerting a force on the implant via the delivery member; and
- moving at least a second portion of the implant from the body lumen via the force.

2. The method of claim 1, exerting the force on the implant further comprises:
- advancing an expandable member into the body lumen;
- transitioning the expandable member to an expanded configuration; and
- advancing the expandable member in the expanded configuration to the implant to exert the force on the implant.

3. The method of claim 1, wherein the body lumen is a first body lumen, the method further comprising:
- conveying a flush solution into the first body lumen to convey the second portion of the implant to a second body lumen.

4. A method of removing an implant from a body lumen, comprising:
- inserting a delivery member into a first body lumen, the delivery member being in fluid communication with an upstream portion of the implant;
- advancing a guidewire through the delivery member and through the implant;
- advancing a microcatheter over the guidewire through the implant;
- positioning a distal end portion of the microcatheter downstream of the implant;
- advancing a retrieval tool through the microcatheter to a position that is downstream of the distal end portion of the microcatheter;
- transitioning the retrieval tool to an expanded configuration;
- engaging a portion of the implant with the retrieval tool in the expanded configuration;
- extracting at least the portion of the implant from the first body lumen by moving the retrieval tool in an upstream direction;
- exerting via the delivery member a force on the upstream portion of the implant; and moving the implant downstream to a second body lumen via the force.

5. The method of claim 4, exerting the force on the upstream portion of the implant further comprises:

advancing an expandable member into the first body lumen;

transitioning the expandable member to an expanded configuration; and advancing the expandable member in a downstream direction to exert the force on the upstream portion of the implant.

6. The method of claim 4, further comprising:

conveying a flush solution into the first body lumen to convey a remnant of the implant downstream to the second body lumen.

* * * * *